US009629673B2

(12) United States Patent
Heilman

(10) Patent No.: US 9,629,673 B2
(45) Date of Patent: Apr. 25, 2017

(54) VARIABLE ANGLE LOCKING SCREW

(71) Applicant: Biomet Manufacturing, LLC, Warsaw, IN (US)

(72) Inventor: Benjamin P Heilman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 914 days.

(21) Appl. No.: 13/921,380

(22) Filed: Jun. 19, 2013

(65) Prior Publication Data

US 2013/0304132 A1 Nov. 14, 2013

Related U.S. Application Data

(62) Division of application No. 12/684,154, filed on Jan. 8, 2010, now Pat. No. 8,486,116.

(51) Int. Cl.
*A61B 17/80* (2006.01)
*F16B 5/02* (2006.01)
*F16B 43/02* (2006.01)
*A61B 17/86* (2006.01)

(52) U.S. Cl.
CPC ...... *A61B 17/8047* (2013.01); *A61B 17/8057* (2013.01); *A61B 17/8685* (2013.01); *F16B 5/0275* (2013.01); *F16B 43/02* (2013.01); *A61B 17/863* (2013.01)

(58) Field of Classification Search
CPC ............ A61B 17/8047; A61B 17/8028; A61B 17/8033; A61B 17/8038
USPC ...................................... 606/70, 71, 280–299
See application file for complete search history.

(56) References Cited

U.S. PATENT DOCUMENTS

| 987,033 | A | 3/1911 | J. Allison |
| 2,230,534 | A | 2/1941 | Elmer et al. |
| 3,069,924 | A | 12/1962 | Watanabee et al. |
| 3,289,522 | A | 12/1966 | Bell |

(Continued)

FOREIGN PATENT DOCUMENTS

| WO | WO 2005/018698 A1 | 3/2005 |
| WO | WO 2010/030845 A1 | 3/2010 |
| WO | WO-2011085272 A1 | 7/2011 |

OTHER PUBLICATIONS

Unknown, VariAx Foot Locking Plate System, c 2007 Stryker, pp. 1-15, Stryker Leibinger GmbH & Co. KG, Germany.

(Continued)

*Primary Examiner* — Matthew Lawson
(74) *Attorney, Agent, or Firm* — Schwegman Lundberg & Woessner, P.A.

(57) ABSTRACT

A method of mounting a base plate to a biologic material comprising inserting and retaining a threaded nut within a first through hole of a base plate, wherein the first hole is at least partially defined by an interior circumferential wall and the threaded nut comprises a cylindrical inner wall at least partially defining a second through hole; inserting a screw through the first and second through holes so that at least a portion of a threaded shaft extends beyond the interior circumferential wall of the base plate; rotating the screw with respect to the base plate and the threaded nut to operatively engage a head of the screw with the threaded nut; inserting the screw into a biologic substrate; and locking an angular orientation of the screw with respect to the base plate.

15 Claims, 36 Drawing Sheets

(56) References Cited

U.S. PATENT DOCUMENTS

| | | |
|---|---|---|
| 3,426,819 A | 2/1969 | Estes et al. |
| 4,006,660 A | 2/1977 | Yamamoto et al. |
| 5,234,431 A | 8/1993 | Keller |
| 5,269,784 A | 12/1993 | Mast |
| 5,326,206 A | 7/1994 | Moore |
| 5,364,399 A | 11/1994 | Lowery et al. |
| 5,456,719 A | 10/1995 | Keller |
| 5,476,880 A | 12/1995 | Cooke et al. |
| 5,482,463 A | 1/1996 | Wilson, Jr. et al. |
| 5,501,684 A | 3/1996 | Schlapfer et al. |
| 5,534,027 A | 7/1996 | Hodorek |
| 5,534,032 A | 7/1996 | Hodorek |
| 5,575,792 A | 11/1996 | Errico et al. |
| 5,578,034 A | 11/1996 | Estes |
| 5,591,234 A | 1/1997 | Kirsch |
| 5,607,428 A | 3/1997 | Lin |
| 5,609,594 A | 3/1997 | Errico et al. |
| 5,690,631 A | 11/1997 | Duncan et al. |
| 5,702,457 A | 12/1997 | Walch et al. |
| 5,776,194 A | 7/1998 | Mikol et al. |
| 5,876,402 A | 3/1999 | Errico et al. |
| 5,931,838 A | 8/1999 | Vito |
| 5,954,722 A | 9/1999 | Bono |
| 5,984,924 A | 11/1999 | Asher et al. |
| 6,004,323 A | 12/1999 | Park et al. |
| 6,030,389 A | 2/2000 | Wagner et al. |
| 6,187,005 B1 | 2/2001 | Brace et al. |
| 6,193,720 B1 | 2/2001 | Yuan et al. |
| 6,206,881 B1 | 3/2001 | Frigg et al. |
| 6,261,291 B1 | 7/2001 | Talaber et al. |
| 6,309,397 B1 | 10/2001 | Julian et al. |
| 6,315,779 B1 | 11/2001 | Morrison et al. |
| 6,322,562 B1 | 11/2001 | Wolter |
| 6,331,179 B1 | 12/2001 | Freid et al. |
| 6,454,769 B2 | 9/2002 | Wagner et al. |
| 6,471,706 B1 | 10/2002 | Schumacher et al. |
| 6,533,786 B1 | 3/2003 | Needham et al. |
| 6,599,290 B2 | 7/2003 | Bailey et al. |
| 6,663,632 B1 | 12/2003 | Frigg |
| 6,663,635 B2 | 12/2003 | Frigg et al. |
| 6,679,883 B2 | 1/2004 | Hawkes et al. |
| 6,692,498 B1 | 2/2004 | Niiranen et al. |
| 6,692,503 B2 | 2/2004 | Foley et al. |
| 6,695,846 B2 | 2/2004 | Richelsoph et al. |
| 6,702,817 B2 | 3/2004 | Beger et al. |
| 6,730,091 B1 | 5/2004 | Pfefferle et al. |
| 6,736,820 B2 | 5/2004 | Biedermann et al. |
| 6,746,453 B2 | 6/2004 | Deloge et al. |
| 6,780,186 B2 | 8/2004 | Errico et al. |
| 6,808,527 B2 | 10/2004 | Lower et al. |
| 6,840,938 B1 | 1/2005 | Morley et al. |
| 6,893,443 B2 | 5/2005 | Frigg et al. |
| 6,955,677 B2 | 10/2005 | Dahners |
| 6,964,664 B2 | 11/2005 | Freid et al. |
| 7,001,387 B2 | 2/2006 | Farris et al. |
| 7,001,389 B1 | 2/2006 | Navarro et al. |
| 7,008,426 B2 | 3/2006 | Paul |
| 7,048,739 B2 | 5/2006 | Konieczynski et al. |
| 7,063,701 B2 | 6/2006 | Michelson |
| 7,063,702 B2 | 6/2006 | Michelson |
| 7,077,844 B2 | 7/2006 | Michelson |
| 7,090,676 B2 | 8/2006 | Huebner et al. |
| 7,097,645 B2 | 8/2006 | Michelson |
| 7,112,202 B2 | 9/2006 | Michelson |
| 7,125,403 B2 | 10/2006 | Julian et al. |
| 7,153,329 B2 | 12/2006 | Wilson |
| 7,169,150 B2 | 1/2007 | Shipp et al. |
| 7,175,624 B2 | 2/2007 | Konieczynski et al. |
| 7,195,633 B2 | 3/2007 | Medoff et al. |
| 7,207,992 B2 | 4/2007 | Ritland |
| 7,229,442 B2 | 6/2007 | Schafer |
| 7,306,597 B2 | 12/2007 | Manzo |
| 7,309,340 B2 | 12/2007 | Fallin et al. |
| 7,314,487 B2 | 1/2008 | Ralph et al. |
| 7,322,983 B2 | 1/2008 | Harris |
| 7,335,205 B2 | 2/2008 | Aeschlimann et al. |
| 7,367,973 B2 | 5/2008 | Manzo et al. |
| 7,399,150 B2 | 7/2008 | Hofschneider |
| 7,410,496 B2 | 8/2008 | Derouet |
| 7,524,325 B2 | 4/2009 | Khalili |
| 7,547,306 B2 | 6/2009 | Michelson |
| 7,637,928 B2 | 12/2009 | Fernandez |
| 7,641,676 B2 | 1/2010 | Mathieu et al. |
| 7,651,497 B2 | 1/2010 | Michelson |
| 7,662,155 B2 | 2/2010 | Metzger et al. |
| 7,678,113 B2 | 3/2010 | Melkent |
| 2002/0029040 A1 | 3/2002 | Morrison et al. |
| 2002/0058939 A1 | 5/2002 | Wagner et al. |
| 2003/0078583 A1 | 4/2003 | Biedermann et al. |
| 2004/0199258 A1 | 10/2004 | Macara |
| 2004/0236330 A1 | 11/2004 | Purcell et al. |
| 2004/0267261 A1* | 12/2004 | Derouet ............ A61B 17/8047 606/70 |
| 2005/0096502 A1 | 5/2005 | Khalili |
| 2005/0143742 A1 | 6/2005 | Porcher |
| 2005/0192571 A1 | 9/2005 | Abdelgany |
| 2005/0192572 A1 | 9/2005 | Abdelgany et al. |
| 2005/0216008 A1 | 9/2005 | Zwirnmann et al. |
| 2005/0251137 A1 | 11/2005 | Ball |
| 2005/0251141 A1 | 11/2005 | Frigg et al. |
| 2005/0273165 A1 | 12/2005 | Griffiths et al. |
| 2006/0016300 A1 | 1/2006 | Bubel |
| 2006/0058797 A1 | 3/2006 | Mathieu et al. |
| 2006/0079884 A1 | 4/2006 | Manzo et al. |
| 2006/0079889 A1 | 4/2006 | Scott |
| 2006/0100626 A1 | 5/2006 | Rathbun et al. |
| 2006/0116678 A1 | 6/2006 | Impellizzeri |
| 2006/0122604 A1 | 6/2006 | Gorhan et al. |
| 2006/0224044 A1 | 10/2006 | Marchek et al. |
| 2006/0235400 A1 | 10/2006 | Schneider |
| 2006/0241618 A1* | 10/2006 | Gasser ............... A61B 17/8047 606/287 |
| 2007/0038214 A1 | 2/2007 | Morley et al. |
| 2007/0055251 A1 | 3/2007 | Huebner et al. |
| 2007/0088360 A1 | 4/2007 | Orbay et al. |
| 2007/0093827 A1 | 4/2007 | Warnick |
| 2007/0162016 A1 | 7/2007 | Matityahu |
| 2007/0162019 A1 | 7/2007 | Burns et al. |
| 2007/0212915 A1 | 9/2007 | Strnad et al. |
| 2007/0270851 A1 | 11/2007 | Erickson et al. |
| 2008/0033437 A1 | 2/2008 | Shipp et al. |
| 2008/0046122 A1 | 2/2008 | Manzo et al. |
| 2008/0114359 A1 | 5/2008 | Murner et al. |
| 2008/0119870 A1 | 5/2008 | Williams |
| 2008/0119895 A1 | 5/2008 | Manceau |
| 2008/0172130 A1 | 7/2008 | Macara |
| 2008/0177291 A1 | 7/2008 | Jensen et al. |
| 2008/0234677 A1 | 9/2008 | Dahners et al. |
| 2008/0234749 A1 | 9/2008 | Forstein |
| 2008/0243141 A1 | 10/2008 | Privitera et al. |
| 2008/0243192 A1 | 10/2008 | Jacene et al. |
| 2008/0281272 A1 | 11/2008 | Blundred et al. |
| 2008/0288000 A1 | 11/2008 | Cawley |
| 2008/0300637 A1 | 12/2008 | Austin et al. |
| 2009/0088807 A1 | 4/2009 | Castaneda et al. |
| 2009/0131938 A1 | 5/2009 | Khatri et al. |
| 2009/0143824 A1 | 6/2009 | Austin et al. |
| 2009/0182337 A1 | 7/2009 | Stopek et al. |
| 2009/0192550 A1 | 7/2009 | Leung et al. |
| 2009/0232618 A1 | 9/2009 | Ballenger |
| 2009/0248087 A1 | 10/2009 | Lewis et al. |
| 2009/0299369 A1 | 12/2009 | Orbay et al. |
| 2010/0011900 A1 | 1/2010 | Burbank |
| 2010/0011901 A1 | 1/2010 | Burbank |
| 2010/0016858 A1 | 1/2010 | Michel |
| 2010/0057127 A1 | 3/2010 | McGuire et al. |

OTHER PUBLICATIONS

Unknown, Cannulated Screws 3.0/3.5/4.0/4.5/6.5/7.0/7.3, c 2004 Stratec Medical, pp. 1-18, Synthes, Oberdorf, Switzerland.
Unknown, Surgical Technique: Lumbar I/F Cage System, c 2002

(56) References Cited

OTHER PUBLICATIONS

DePuy AcroMed, pp. 1-21, DePuy AcroMed, Inc., Raynham, Massachusetts.

Larson et al., Locking Plate Technology and Its Applications in Upper Extremity Fracture Care, Hand Clinics 23 (2007) 269-278, c 2007, Elsevier Inc., USA.

International Search Report and Written Opinion for PCT/US2011/020607 dated May 12, 2011, 25 pages.

International Preliminary Report on Patentability for PCT/US2011/020607 dated Jul. 10, 2012, 21 pages.

"U.S. Appl. No. 12/684,154, Examiner Interview Summary mailed May 16, 2013", 2 pgs.

"U.S. Appl. No. 12/684,154, Non Final Office Action mailed Nov. 6, 2012", 11 pgs.

"U.S. Appl. No. 12/684,154, Notice of Allowance mailed Apr. 16, 2013", 12 pgs.

"U.S. Appl. No. 12/684,154, Response filed Feb. 27, 2013 to Non Final Office Action mailed Nov. 6, 2012", 14 pgs.

"U.S. Appl. No. 12/684,154, Response filed Aug. 22, 2012 to Restriction Requirement mailed Aug. 13, 2012", 9 pgs.

"U.S. Appl. No. 12/684,154, Restriction Requirement mailed Aug. 13, 2012", 8 pgs.

"International Application Serial No. PCT/US2011/020607, Invitation to Pay Additional Fees mailed Feb. 28, 2011", 2 pgs.

\* cited by examiner

VARIABLE ANGLE LOCKING SCREW

CROSS-REFERENCE TO RELATED APPLICATIONS

This application is a divisional of U.S. patent application Ser. No. 12/684,154, filed Jan. 8, 2010, and entitled "Variable Angle Locking Screw," the disclosure of which is expressly incorporated in its entirety herein by this reference.

FIELD OF THE INVENTION

The present disclosure relates to retention devices for surgical procedures and, more specifically, relates to variable angle retention devices to mount bone to a plate material.

INTRODUCTION TO THE INVENTION

It is a first aspect of the present invention to provide an implantable orthopedic fastener comprising: (a) a support substrate including a first through hole at least partially defined by an interior wall tapering to decrease a diameter of the first through hole; (b) a nut having an internal wall at least partially defining a second through hole having a diameter less than the diameter of the first through hole, the nut also including a projection radially extending beyond the internal wall to provide the nut with a widthwise dimension greater than the diameter of the first through hole, the nut further including a washer radially extending beyond the internal wall, the washer having a widthwise dimension greater than the diameter of the first through hole, where the projection and the washer cooperate to retain at least a portion of the nut within the first through hole; and (c) a fastening screw comprising a head and a longitudinal shaft extending from the head, the longitudinal shaft including external threads sized to permit through passage of the longitudinal shaft with respect to first and second through holes, the head also including a cap sized to allow entry of the head into the first through hole but prohibiting through passage of the head with respect to the first through hole, the cap further including an opening into a hollow formed into a top of the head, where at least one of the head and internal wall of the nut includes threads to selectively mount the fastening screw to the nut, the threads operative to allow rotational and vertical motion of the fastening screw with respect to the nut, and where the support substrate, the nut, and the fastening screw cooperate to form a compression joint operatively sandwiching at least a portion of the interior wall between the cap and the washer of the nut to fix an angular orientation of the fastening screw with respect to the support substrate.

In a more detailed embodiment of the first aspect, the internal wall of the nut includes internal threads, the head of the fastening screw includes external threads, and the external threads of the head are adapted to interface with the internal threads of the nut. In yet another more detailed embodiment, the projection comprises a collar at least partially circumscribing the internal wall of the nut. In still a further detailed embodiment, the collar is separable from the nut. In a more detailed embodiment, the nut includes a detent at least partially circumscribing the internal wall, the detent having a widthwise dimension less than the diameter of the first through hole, and the collar includes a circumferential shelf to receive the detent of the nut and operatively couple the collar to the nut. In a more detailed embodiment, the head includes external threads, and a vertical spacing between individual threads of the external threads of the head is less than a vertical spacing between individual threads of the external threads of the longitudinal shaft. In another more detailed embodiment, the head includes external threads, and a diameter of the external threads of the head is greater than a diameter of the external threads of the longitudinal shaft. In still another more detailed embodiment, the hollow of the head is at least partially defined by a conical depression, and the hollow is sized to receive a driver to rotate the screw in at least one of a clockwise direction and a counterclockwise direction.

In yet another more detailed embodiment of the first aspect, the cap exhibits a circular horizontal cross-section, the cap includes an overhang extending radially outward from the screw, and a diameter of the cap is larger than the diameter of the first through hole. In still another more detailed embodiment, a contact surface of the interior wall of the support substrate is at least one of bowl shaped and linearly sloped, a contact surface of the projection is at least one of bowl shaped and linearly sloped, and the contact surface of the projection is adapted to engage the contact surface of the interior wall. In a further detailed embodiment, the support substrate includes a first surface and a second surface, the first through hole extends through the first surface and the second surface, and the second surface includes an opening extending into the support substrate that at least partially defines a cavity that at least partially circumscribes the first through hole. In still a further detailed embodiment, the first through hole is at least partially defined by a circumferential flange, the circumferential flange including the interior wall tapering to decrease the diameter of the first through hole, the support substrate includes an inner wall at least partially defining the cavity of the support substrate, and a terminal end of the circumferential flange is spaced apart from the inner wall of the support substrate to delineate a circumferential cavity at least partially extending around a portion of the circumferential flange. In a more detailed embodiment, the washer of the nut includes a circumferential discontinuity, the support substrate includes a stop, and the stop is received within the circumferential discontinuity of the washer to inhibit rotation of the nut with respect to the support substrate. In a more detailed embodiment, the nut includes a hollow cylinder that defines the second through hole, the hollow cylinder including a first end axially spaced apart from a second end, where the projection is mounted to the hollow cylinder proximate the first end and the washer is mounted to the hollow cylinder proximate the second end so that the projection and washer are axially spaced apart. In another more detailed embodiment, the projection comprises a plurality of projections that are circumferentially spaced apart from one another.

It is a second aspect of the present invention to provide an implantable orthopedic fastener comprising: (a) a support substrate including a first surface generally opposite a second surface, the first surface including an opening that at least partially defines a tapered flange at least partially defining a first through hole extending through the support substrate, the second surface including an opening leading into a cavity at least partially circumscribing the first through hole and the tapered flange; (b) a nut comprising an interior circumferential wall at least partially defining a second through hole having a diameter less than a diameter of the first through hole, the interior circumferential wall including threads, and the nut including a circumferential recess receiving at least a portion of the tapered flange; and (c) a fastening screw comprising a head and a longitudinal shaft extending from the head, the longitudinal shaft including threads sized to permit through passage of the longitudinal shaft with respect to the first and second through holes, the head sized to allow entry of the head into the first hole, but prohibiting passage of the head beyond the first through hole, the head also including circumferential threads sized to engage the threads of the nut, where the support substrate includes a first anti-rotation feature operative to inhibit rotation of the nut with respect to the support substrate.

In a more detailed embodiment of the second aspect, the nut includes a projection radially extending beyond the interior circumferential wall to provide the nut with a widthwise dimension greater than the diameter of the first through hole, the nut includes a washer radially extending beyond the interior circumferential wall, the washer having a widthwise dimension greater than the diameter of the first through hole, and the projection and washer cooperate to retain at least a portion of the nut within the first through hole. In yet another more detailed embodiment, the projection comprises a collar at least partially circumscribing the interior circumferential wall of the nut. In a further detailed embodiment, the collar is separable from the nut. In still a further detailed embodiment, the nut includes a detent at least partially circumscribing the interior circumferential wall, the detent having a widthwise dimension less than the diameter of the first through hole, and the collar includes a shelf at least partially circumscribing the interior circumferential wall, the shelf adapted to receive the detent of the nut to operatively couple the collar to the nut. In a more detailed embodiment, the projection comprises a plurality of projections that are circumferentially spaced apart from one another.

It is a third aspect of the present invention to provide an implantable orthopedic fastener comprising: (a) a support substrate including an internal circumferential wall at least partially defining a first through hole, the support substrate including a locking ring channel; (b) a threaded washer at least partially defining a second through hole and sized to be received within the first through hole of the support substrate, but the size of the threaded washer prohibits egress of the threaded washer completely through the first through hole; (c) a locking ring at least partially defining a third through hole and adapted to be received within the locking ring channel of the support substrate; and (d) a fastening screw comprising a head and a longitudinal shaft, the longitudinal shaft including threads sized to permit through passage of the longitudinal shaft with respect to first, second, and third through holes, the head sized to allow entry of the head into the first hole and the second hole, and allowing passage of the head through the third hole, but the size of the head prohibits egress of the head completely through the first through hole, where at least one of the threaded washer and the support substrate includes an anti-rotation feature operative to inhibit rotation of the threaded washer with respect to the support substrate, where the threaded washer includes threads adapted to interface with circumferential threads of the head of the fastening screw to couple the threaded washer to the fastening screw, and where the locking ring prohibits removal of the threaded washer from the first through hole.

In a more detailed embodiment of the third aspect, the threaded washer includes a projection, the internal circumferential wall includes an indentation adapted to receive the projection of the threaded washer, and the projection and the indentation comprise the anti-rotation feature operative to inhibit rotation of the threaded washer with respect to the support substrate. In yet another more detailed embodiment, the anti-rotation feature comprises a follower and track engagement between the threaded washer and the support substrate in which the follower and the track are sized so that the follower engages the track and restrains the threaded washer from spinning within the first through hole. In a further detailed embodiment, the threaded washer includes at least one follower that engages the track formed within the support substrate. In still a further detailed embodiment, the support substrate includes at least one follower that engages the track formed within the threaded washer. In a more detailed embodiment, the invention further includes a washer at least partially defining a fourth through hole and sized to be received within the first through hole of the support substrate, but the size of the washer prohibits egress of the washer completely through the first through hole, where the longitudinal shaft of the fastening screw is sized to permit through passage of the longitudinal shaft with respect to fourth through hole, but the size of the head of the fastening screw prohibits passage of the head with respect to the fourth through hole. In a more detailed embodiment, the internal circumferential wall includes a circumferential taper that prohibits passage of the washer with respect to the first through hole. In another more detailed embodiment, an internal wall of the washer that partially defines the fourth through opening is tapered, and a transition between the head and the longitudinal shaft of the fastening screw is tapered to decrease a diameter of the fastening screw. In yet another more detailed embodiment, the locking ring, fastening screw, washer, threaded washer, and support substrate create a compression joint that forces the washer against the support substrate when the threaded washer is forced against the locking ring as the head of the fastening screw is rotated within the second through hole.

It is a fourth aspect of the present invention to provide an implantable orthopedic fastener comprising: (a) a support substrate including an internal circumferential wall at least partially defining a first through hole, the internal circumferential wall including a first anti-rotation feature and a second anti-rotation feature different from the first anti-rotation feature; (b) a threaded washer comprising a wall at least partially defining a second through hole, the wall including an internal surface having threads and an external surface including a third anti-rotation feature, the threaded washer sized to be received within the first through hole of the support substrate; (c) a locking ring including a semi-circular wall at least partially defining a third through hole, the locking ring including a fourth anti-rotation feature; and (d) a fastening screw comprising a head and a longitudinal shaft extending from the head, the longitudinal shaft including threads sized to permit through passage of the longitudinal shaft with respect to first, second, and third through holes, the head sized to allow entry of the head into the first through hole and the second through hole, and allowing passage of the head through the third through hole, but prohibiting passage of the head with respect to the first through hole, the head also including circumferential threads sized to engage the threads of the threaded washer, where the combination of the first anti-rotation feature and the third anti-rotation feature inhibit rotation of the threaded washer with respect to the internal circumferential wall of the support substrate, but permit axial motion of the threaded washer with respect to the internal circumferential wall of the support substrate, and where the combination of the second anti-rotation feature and the fourth anti-rotation feature inhibit rotation and axial motion of the locking ring with respect to the internal circumferential wall of the support substrate.

In a more detailed embodiment of the fourth aspect, the threaded washer includes a protrusion comprising the third anti-rotation feature, the internal circumferential wall includes an indentation adapted to receive the protrusion of the threaded washer, and the indentation comprises the first anti-rotation feature. In yet another more detailed embodiment, the first anti-rotation feature and the third anti-rotation feature comprises a follower and track engagement between the threaded washer and the support substrate in which the follower and the track are sized so that the follower engages the track and restrains the threaded washer from rotation within the first through hole. In a further detailed embodiment, the threaded washer includes the follower that engages the track formed within the support substrate. In still a further detailed embodiment, the support substrate includes the follower that engages the track formed within the threaded washer. In a more detailed embodiment, a washer at least partially defining a fourth through hole and sized to be received within the first through hole of the support substrate, but prohibiting egress of the washer completely through the first through hole, where the longitudinal shaft of the fastening screw is sized to permit through passage of the longitudinal shaft with respect to fourth through hole, but the head of the fastening screw is sized prohibit passage of the head with respect to the fourth through hole. In a more detailed embodiment, the internal circumferential wall includes a circumferential taper that prohibits passage of the washer completely through the first through hole. In another more detailed embodiment, the locking ring, fastening screw, washer, threaded washer, and support substrate create a compression joint that forces the washer against the support substrate when the threaded washer is forced against the locking ring as the head of the fastening screw is rotated within the second through hole.

It is a fifth aspect of the present invention to provide a method of mounting a base plate to a biologic material, the method comprising: (a) inserting and retaining a threaded nut within a first through hole of a base plate, the first hole at least partially defined by an interior circumferential wall, the base plate including a first anti-rotation feature, and the threaded nut comprising: (1) a cylindrical inner wall at least partially defining a second through hole, and (2) an engaging wall extending radially and proximate an end of the threaded nut and at least partially circumscribing and extending toward an opposing end of the threaded nut, where the threaded nut is axially repositionable and selectively rotatable within the first through hole of the base plate, and where the threaded nut includes a second anti-rotation feature adapted to selectively engage the first anti-rotation feature of the base plate to inhibit rotation of the threaded nut with respect to the base plate; (b) inserting a screw through the first and second through holes so that at least a portion of a threaded shaft extends beyond the interior circumferential wall of the base plate, where at least a portion of the screw is maintained within the first and second through holes, and where the screw has angular freedom other than being coaxial with the first hole; (c) rotating the screw with respect to the base plate and the threaded nut to operatively engage a head of the screw with the threaded nut, where continued rotation of the screw after engagement between the head and the threaded nut is operative to axially reposition the threaded nut along a length of the screw; (d) inserting the screw into a biologic substrate; and (e) locking an angular orientation of the screw with respect to the base plate by axially repositioning the threaded nut via rotation of the screw so the engaging wall of the threaded nut and the head of the screw sandwich a flange of the base plate to form a compression joint, where the flange at least partially defines the first hole.

It is a sixth aspect of the present invention to provide a method of mounting a base plate to a biologic material, the method comprising: (a) mounting a threaded nut to a base plate so the threaded nut is axially and angularly repositionable with respect to the base plate, but the threaded nut remains mounted to the base plate, the base plate including a first through hole at least partially occupied by the threaded nut, the threaded nut including a second through hole; (b) inserting at least a portion of a threaded shaft of a screw through the first and second through holes so that some of the threaded shaft extends beyond the base plate, wherein at least a segment of the screw is maintained within the first and second through holes, and wherein the threaded shaft has axial and angular freedom with respect to the first and second through holes; (c) initially rotating the screw with respect to the base plate and the threaded nut so that the screw becomes coupled to the threaded nut, where, upon initial rotation, the threaded shaft continues to have angular freedom with respect to the first through hole; and (d) continuing rotating the screw with respect to the threaded nut to axially reposition the threaded nut along a portion of the screw and concurrently insert the screw into a biologic substrate, whereby rotation of the screw ultimately causes the screw and threaded nut to sandwich a portion of the base plate therebetween such that the threaded nut, screw, and the portion of the base plate form a compression joint that discontinues the angular freedom of the threaded shaft with respect to the first through hole.

It is a seventh aspect of the present invention to provide a method of mounting a base plate to a biologic material, the method comprising: (a) inserting a threaded washer within a first through hole of a base plate, the first hole at least partially defined by an interior circumferential wall, and the threaded washer defining a second through hole; (b) inserting a locking ring within the first hole of the base plate, the locking ring being seated within a groove formed within the interior circumferential wall, and the locking ring at least partially defining a third through hole; (c) inserting at least a portion of a threaded shaft of a screw through the first, second, and third through holes so that some of the threaded shaft extends beyond the interior circumferential wall of the base plate, where at least a portion of the screw is maintained within the first through hole, and wherein the screw has angular freedom other than being coaxial with the first and second through holes; (d) initially rotating the screw with respect to the base plate and threaded nut so that the screw becomes coupled to the threaded nut, where, upon initial rotation, the threaded shaft has angular freedom with respect to the first through hole; and (e) continuing rotation of the screw with respect to the threaded nut to axially reposition the threaded nut along a portion of the screw and concurrently insert the screw into a biologic substrate, whereby rotation of the screw ultimately causes the threaded nut to be forced against the locking ring, thereby discontinuing the angular freedom of the threaded shaft with respect to the first through hole.

DETAILED DESCRIPTION

The exemplary embodiments of the present disclosure are described and illustrated below to encompass retention devices for surgical procedures and methods of fabricating the retention devices and using the retention devices in a surgical procedure. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
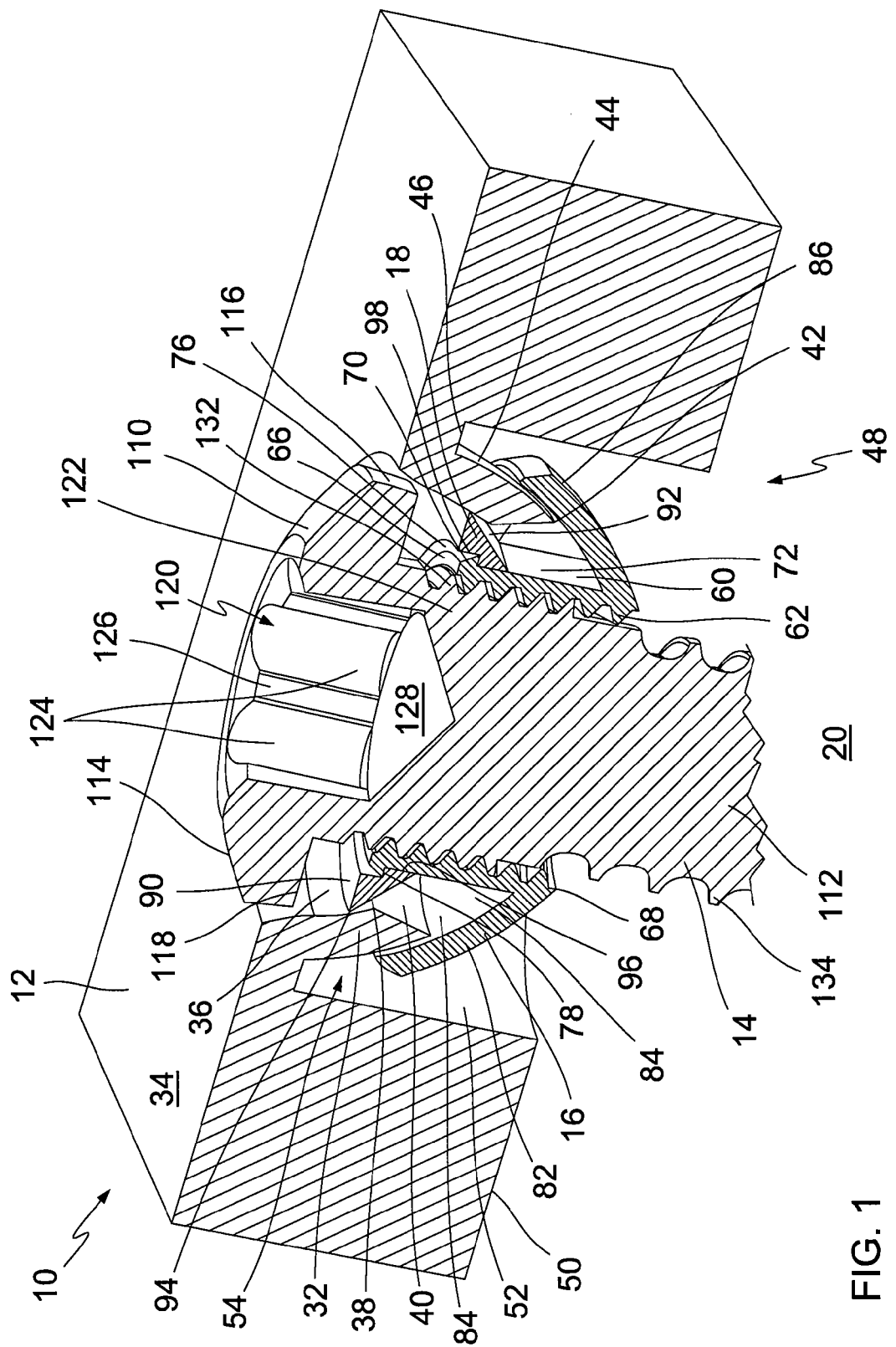
FIG. 1 is an elevated, perspective, cross-sectional view of a first exemplary embodiment of the instant disclosure.
Figure 2:
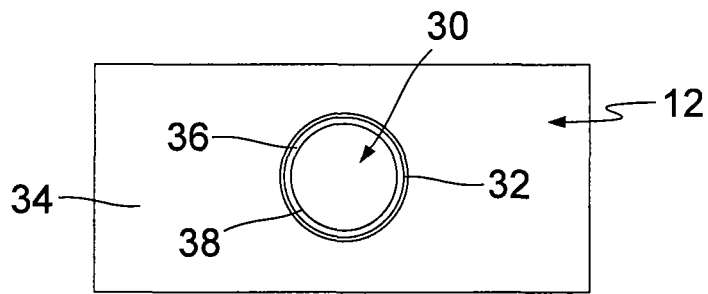
FIG. 2 is a top view of an exemplary plate in accordance with the instant disclosure.
Figure 3:
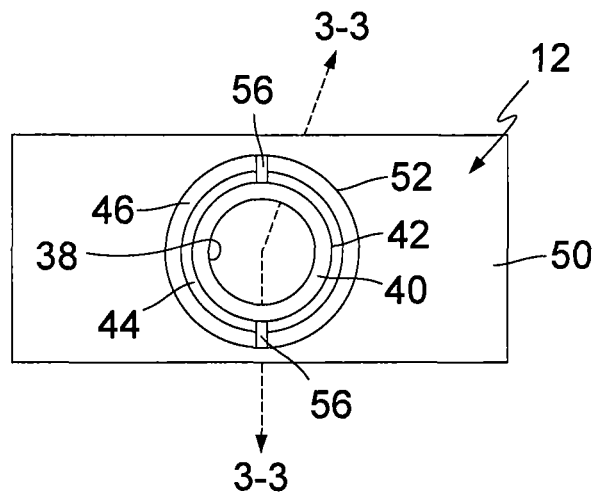
FIG. 3 is a bottom view of the exemplary plate of FIG. 2.
Figure 4:
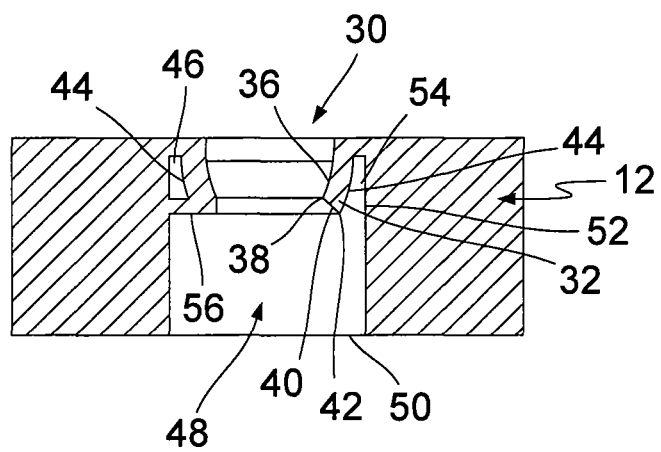
FIG. 4 is a cross-sectional view of the exemplary plate of FIG. 3 taken along lines 3-3.
Figure 5:
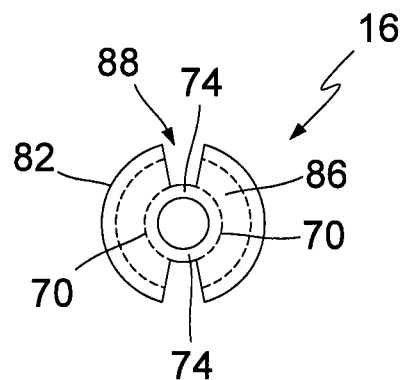
FIG. 5 is a bottom of an exemplary threaded nut in accordance with the instant disclosure.
Figure 6:
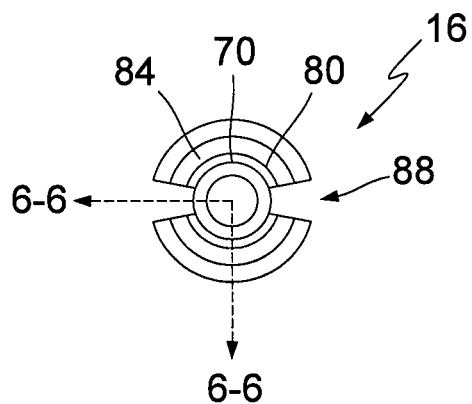
FIG. 6 is a top view of the exemplary threaded nut of FIG. 5.
Figure 7:
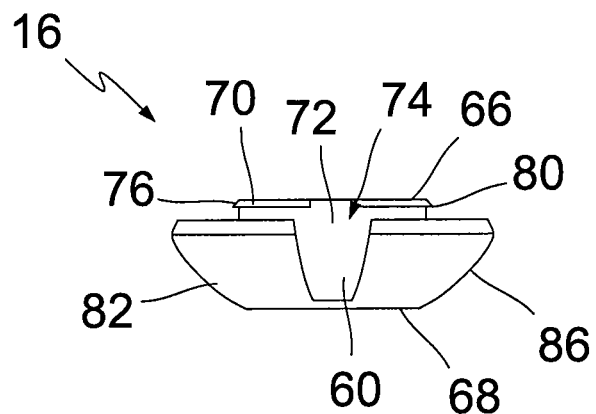
FIG. 7 is a profile view of the exemplary threaded nut of FIG. 5.
Figure 8:
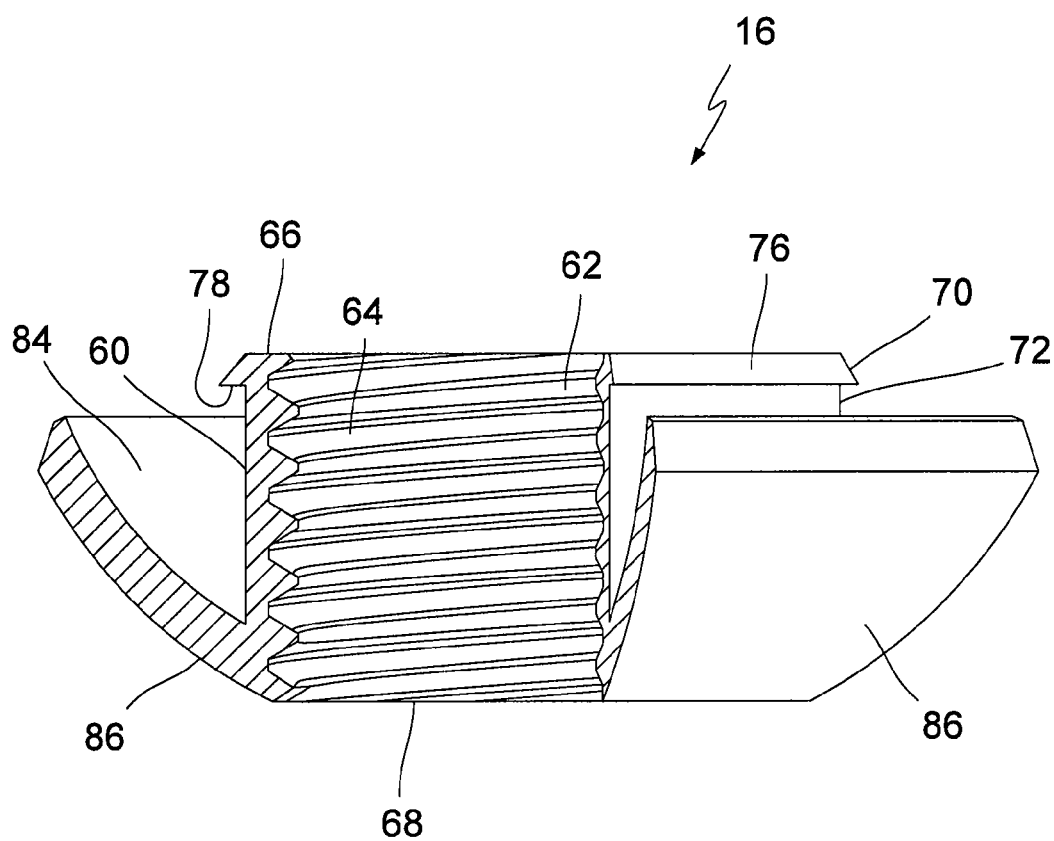
FIG. 8 is a cross-sectional view of the exemplary threaded nut of FIG. 6 taken along line 6-6.
Figure 9:
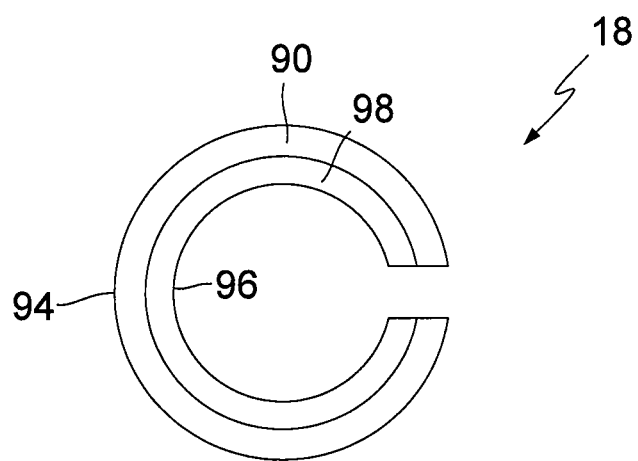
FIG. 9 is a top view of an exemplary retention ring in accordance with the instant disclosure.
Figure 10:
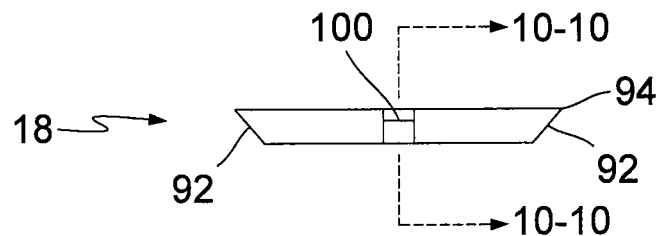
FIG. 10 is a profile view of the exemplary retention ring of FIG. 9.
Figure 11:
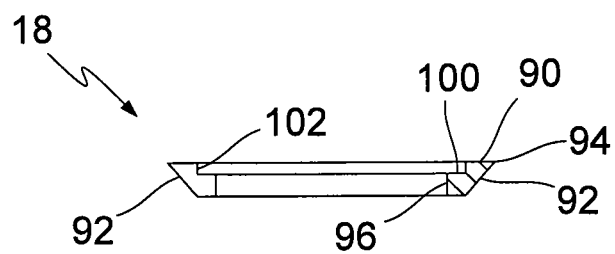
FIG. 11 is a cross-sectional view of the exemplary retention ring of FIG. 10 taken along line 10-10.
Figure 12:
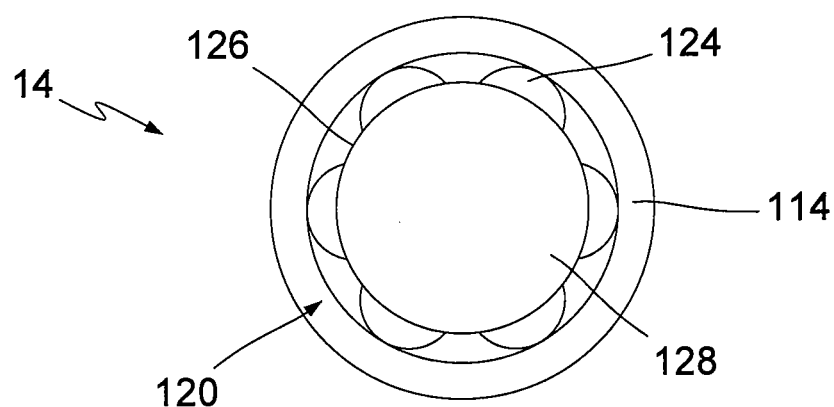
FIG. 12 is a top view of an exemplary screw in accordance with the instant disclosure.
Figure 13:
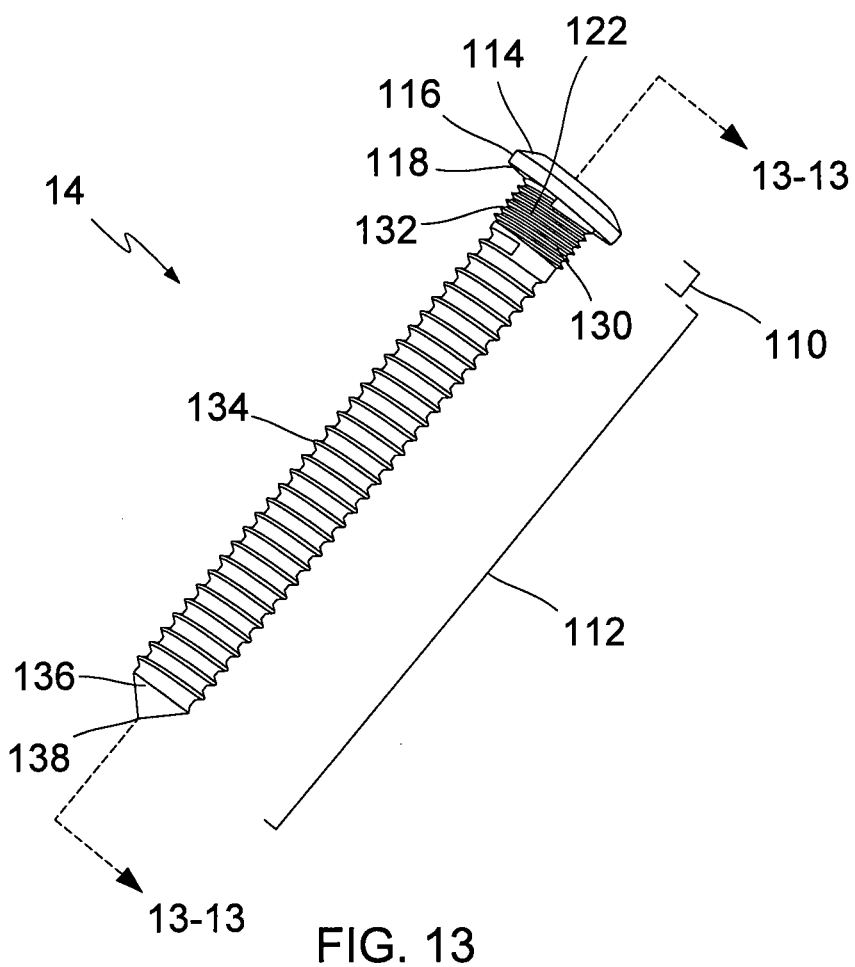
FIG. 13 is a profile view of the exemplary screw of FIG. 12.
Figure 14:
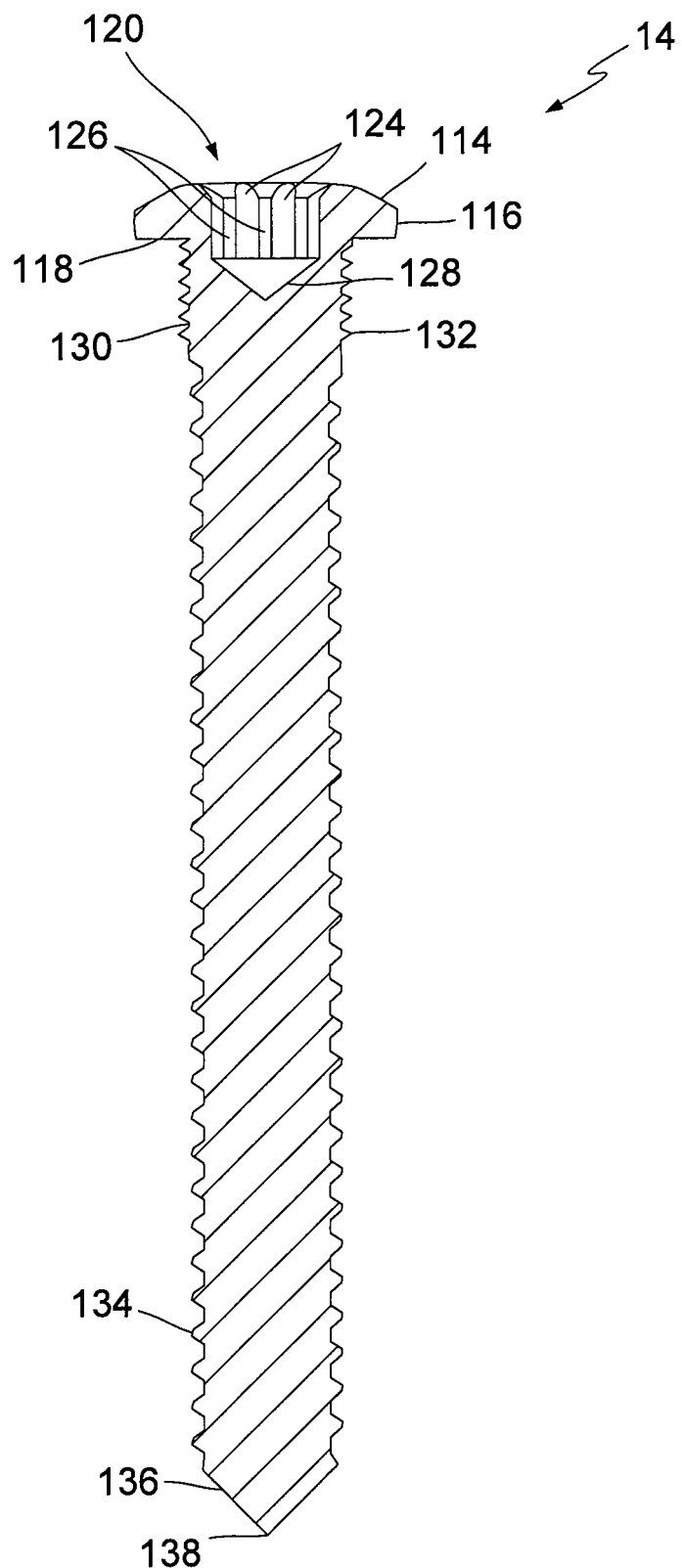
FIG. 14 is a cross-sectional view of the exemplary screw of FIG. 13 taken along line 13-13.
Figure 15:
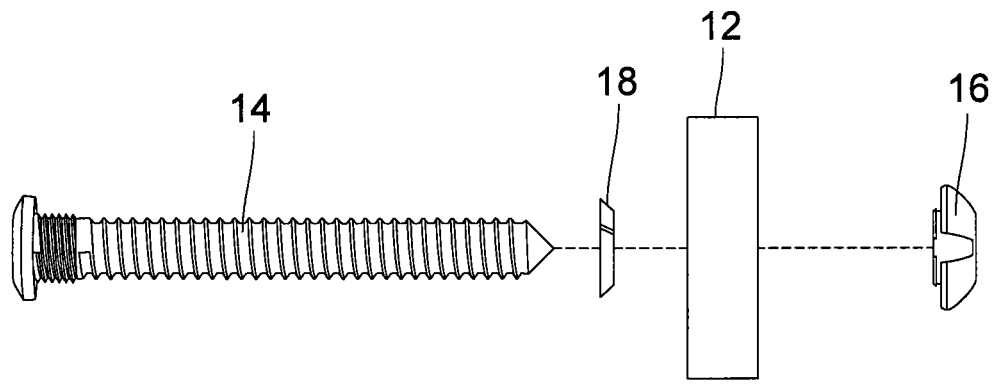
FIG. 15 is an exploded view of the first exemplary embodiment of FIG. 1.
Figure 16:
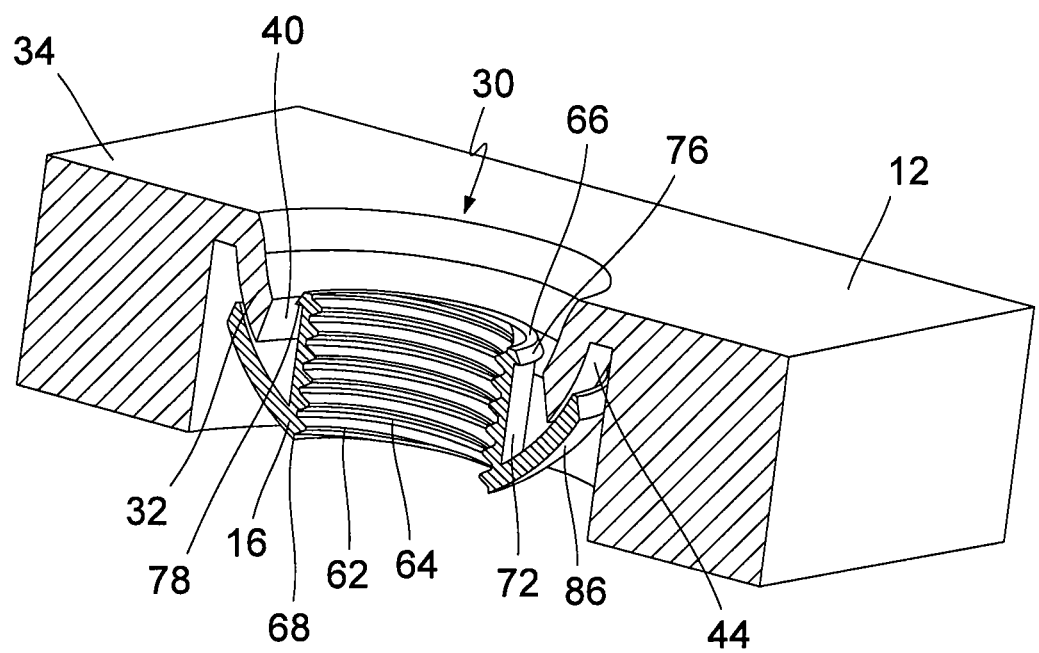
FIG. 16 is a cross-sectional view of the first exemplary embodiment of FIG. 1, without the retention ring and screw.

Referencing FIG. 1, a first exemplary variable angle locking screw assembly 10 comprises a base plate 12, a screw 14, a washer nut 16, and a retention ring 18. These components cooperate to retain the screw 14 at one of a multitude of predetermined angles with respect to the base plate 12 when the screw is mounted to a biologic substrate 20, such as human bone, and the screw 14 is tightened with respect to the other components of the variable angle locking screw assembly 10.

Referring specifically to FIGS. 1-4, the base plate 12 includes at least one through opening 30 adapted to allow throughput of the shaft of the screw 14, while inhibiting throughput of the head of the screw. In this exemplary embodiment, the through opening 30 is partially defined by an annular flange 32 that extends vertically downward from a top surface 34 of the base plate 12. An upper surface 36 of the flange 32 is arcuate and operates to create a bowl-shaped depression within the top surface 34 that funnels the screw into the through opening 30. As a result, a narrowest portion of the through opening 30 is defined by a leading edge 38 of the flange 32. This leading edge 38 transitions into a back-cut face 40 having a trailing edge 42 that is positioned radially outside of and axially below the leading edge 38. In other words, the diameter of the through opening 30 at the leading edge 38 is less than the diameter of the through opening 30 at the trailing edge 42. As will be discussed in more detail below, the back-cut face 40 provides for a range of angles that the screw may be oriented other than perpendicular (i.e., coaxial) with respect to the through opening 30.

The trailing edge 42 transitions into an arcuately shaped underneath surface 44 of the flange 32 that intersects a horizontal surface 46 of a cavity 48 formed within a bottom surface 50 of the base plate 12. The cavity 48 is generally circular in horizontal cross-section (see FIGS. 3 and 4) and is defined by a circumferential vertical wall 52 extending into the interior of the plate material. This circumferential vertical wall 52 co-axially outlies the through opening 30 formed within the top surface 34 of the base plate 12. Consequently, the circumferential vertical wall 52, the horizontal surface 46, and the underneath surface 44 of the flange 32 cooperate to define a recess 54 adapted to receive a portion of the washer nut 16. Within the recess 54 are at least two radially extending stops 56 bridging between the circumferential vertical wall 52 and the flange 32 that are equidistantly spaced from one another and adapted to interact with features on the washer nut 16 to selectively inhibit rotation of the washer nut with respect to the base plate 12 as will be discussed below.

Referencing FIGS. 1 and 5-8, the washer nut 16 includes a hollow cylinder 60 having internal threads 62 formed into or extending from an interior surface 64 of the cylinder. As will be discussed in more detail below, these threads 62 are adapted to interface with threads formed into or extending from the screw 14. The cylinder 60 also includes an upper end 66, opposite a lower end 68, having a discontinuous lip 70 that extends radially from an exterior surface 72 of the cylinder 60. In this exemplary embodiment, the lip 70 includes two sections, with each section being equidistantly spaced and extending approximately 160 degrees around the cylinder 60, thereby leaving two gaps 74 between the lip sections. The lip 70 includes a sloped surface 76 sloping downward from the cylinder 60 and a lower horizontal surface 78 that converge at a point 80, with the point being the farthest radially from the center of the cylinder 60. The lower horizontal surface 78 of the lip 70 intersects the generally smooth, exterior surface 72 of the cylinder 60 proximate the upper end 66.

The lower end 68 of the cylinder 60 includes a discontinuous dome-shaped washer 82 arcuately extending radially outward from the cylinder 60 and vertically toward the upper end 66. The dome-shaped washer 82 includes opposed concave and convex surfaces 84, 86, where the concave surface generally faces the lip 70. In this exemplary embodiment, the dome-shaped washer 82 includes two circumferential sections, with each section being equidistantly spaced and extending approximately 160 degrees around the cylinder 60, thereby leaving two circumferential spaces 88 between the washer sections. Both gaps 74 between the lip 70 sections and the spaces 88 between the washer 82 sections are radially aligned, where the spaces are adapted to selectively receive the radially extending stops 56 of the plate material to inhibit rotation of the washer nut 16 with respect to the base plate 12, presuming the retention ring 18 is in place.

Referring to FIGS. 1 and 9-11, the retention ring 18 comprises a discontinuous circular ring adapted to reside within the bowl-shaped depression 36 within the top surface of the base plate 12 (created by the flange 32) and to engage the lip 70 of the washer nut 16 in order to retain at least a portion of the washer nut within the through opening 30. The discontinuity of the retention ring 18 allows the ring to be deformed slightly. A top surface 90 of the retention ring in the present embodiment is generally planar and meets an outer sloped surface 92 at a circumferential point 94, and sloped downwardly and radially inward from the point 94. As will be discussed in more detail below, the angular orientation of the sloped surface 92 may match that of the upper surface 36 of the flange 32 or may differ from the angular orientation of the upper surface of the flange. The circumferential point 94 defines the outer diameter of the retention ring 18, in contrast to the inner diameter of the retention ring that is defined by an interior wall 96. The angular orientation of the interior wall 96 is adapted to approximate the angular orientation of the smooth exterior surface 72 of the cylinder 60. This interior wall 96 and the top surface 90 are interposed by a circumferentially extending step 98 formed into the top surface retention ring 18 and extending radially from the interior wall 96. The step 98 comprises a horizontal surface 100 and a vertical surface 102. As discussed above, the inner diameter of the step 98 is defined by the boundary of the interior wall 96, where the inner diameter is slightly larger than the outer diameter of the cylinder 60. As will be discussed in more detail below, the horizontal surface 100 of the retention ring 18 is adapted to engage the horizontal lip surface 78 of the washer nut 16 in order to retain at least a portion of the washer nut within the through opening 30 as the screw 14 is inserted and tightened.

Referencing FIGS. 1 and 12-14, the screw 14 comprises a head 110 and a shaft 112 extending from the head. The head 110 comprises a dome 114 that transitions into a vertical circumferential surface 116. This vertical circumferential surface 116 transitions into an underneath planar surface 118 on the bottom of the head 110. Opposite the bottom of the head 110 is an opening 120 formed at the apex of the dome 114. The opening 120 extends through the head 110 and into a head end 122 of the shaft 112. In exemplary form, the opening 120 is defined by a series of six alternating semicircular walls 124 and six straight walls 126 that form a hexagonal pattern. At the base of the walls 124, 126 is a conical wall 128 that defines a conical part of the opening 120 terminating in the head end 122 of the shaft 112. An exterior surface 130 of the head end 122 of the shaft 112 includes threads 132 that are adapted to engage the threads 62 of the washer nut 16. These threads 132 extend along a predetermined longitudinal section of the shaft 112 and transition into a second set of threads 134 adapted to engage the biologic substrate 20. The second set of threads 134 extends along the shaft until reaching a conical projection 136 at an opposite end 138 of the screw 14.

Referencing FIGS. 1-16, the first exemplary variable angle locking screw assembly 10 may be utilized to secure the biologic substrate 20, such as human bone, in a constant position for proper healing. An exemplary procedure for securing the substrate 20 to the base plate 12 may include drilling a hole into the substrate 20, where the hole has a diameter less than the diameter of the second set of threads 134 on the opposite end 138 of the screw 14. Prior to drilling the hole into the substrate 20, the washer nut 16 has already been mounted within the cavity 48 of the base plate 12 using the retention ring 18.

By way of example, the washer nut 16 is oriented so that the upper end 66 of the cylinder 60 is inserted initially into the cavity 48 of the base plate 12, followed by the washer 82 end of the washer nut. At generally the same time, the spaces 88 between the washer 82 sections are aligned to receive the radially extending stops 56 located within the cavity 48. The cylinder 60 is moved further into the cavity 48 so that the leading edge 38 of the flange 32 circumscribes the exterior surface 72 of the cylinder 60 and the lip 70 extends upward beyond the leading edge. Likewise, the spaces 88 between the washer 82 sections receive the radially extending stops 56. To ensure the cylinder 60 is sufficiently inserted upward into the through opening 30, the concave surface 84 of the washer 82 may contact the underneath surface 44 of the flange 32. In this orientation, the retention ring 18 may be inserted within the through opening 30 in the top surface 34 of the base plate 12 and expanded to increase the internal diameter sufficient to allow the interior surface of the ring to pass beyond the point 80 of the washer nut 16 lip 70. The sloped surface 76 of the lip 70 acts to cam the ring 18 radially outward as the ring and washer nut 16 are forced axially towards one another. After passing beyond the point 80, the retention ring 18 may be allowed to return to its default orientation. This default orientation of the ring 18 exhibits an internal diameter that is less than the outside diameter of the lip 70 as measured across the point 80. After the ring 18 has returned to its default orientation, the upper horizontal surface 100 of the retention ring step 98 is below the lower horizontal lip surface 78 of the washer nut 16. Thereafter, the force retaining the concave surface 84 of the washer 82 against the underneath surface 44 of the flange 32 may be released. Releasing this temporary retention force causes the cylinder 60 to move downward, toward the bottom surface 50 of the base plate 12 so that the lower horizontal lip surface 78 of the washer nut 16 contacts and rides upon the upper horizontal surface 100 of the retention ring 18 step 98, thereby retaining a portion of the cylinder 60 within the through opening 30. At the same time, releasing this temporary retention force causes the concave surface 84 of the washer 82 to no longer contact the underneath surface 44 of the flange 32. But, the spaces 88 between the washer 82 sections continue to receive the radially extending stops 56. In this exemplary embodiment, the outside diameter of the retention ring 18 is greater than the diameter of the through opening 30 at the leading edge 38 of the flange 32 so that the sloped surface 92 of the ring contacts the upper surface 36 of the flange, which operates to retain a portion of the cylinder 60 within the through opening 30.

After the retention ring 18 and washer nut 16 are mounted to one another, thereby mounting the washer nut 16 to the base plate 12, a surgeon may then insert a drill bit (not shown) into the through hole 30 and into an opening defined by the hollow cylinder 60 in order for the drill bit to contact the biologic substrate 20, such as human bone. At this time, the surgeon controls the drill bit to create a hole within the substrate 20 that will ultimately receive the screw 14 in order to mount the base plate 12 to the substrate 20. After the drill bit has completed boring the hole within the substrate 20, the drill bit is withdrawn from the substrate 20, from the through hole 30, and from the hollow cylinder 60.

After removing the drill bit, the screw 14 may be inserted into the through hole 30 and into the hollow cylinder 60 at a desired angular orientation (up to approximately 15 degrees or greater from axial alignment with the through hole 30), with the opposite end 138 of the shaft 112 being inserted first. Specifically, the opposite end 138 of the shaft 138 and the second set of threads 134 are sized to pass into the hollow cylinder 60 without engaging the threads 62 on the interior surface 64 of the cylinder. As the shaft 112 of the screw 14 continues to be inserted and travel through the through hole 30 and into and beyond the hollow cylinder 60, ultimately the head end 122 of the shaft reaches the hollow cylinder 60 at approximately the same time as the conical projection 136 at the opposite end 138 of the screw 14 reaches the previously drilled hole in the substrate 20.

After the screw 14 has been angularly oriented and aligned with the previously drilled hole into the biologic substrate 20, the screw 14 may be tightened and in so doing, retain the angular position of the screw. This may be accomplished by rotating the screw 14 in a clockwise direction so that the threads 132 at the head end 122 engage the threads 62 on the interior of the cylinder 60 to couple the screw 14 to the washer nut 16. At the same time, clockwise rotation of the screw 14 is operative to engage the second set of threads 134 with the biologic substrate 20. As the screw 14 is rotated in a clockwise direction (between 1-3 turns, for example), the stops 56 of the base plate 12 continue to be received within the spaces 88 of the washer 82 to inhibit rotation of the washer nut 16 with respect to the base plate 12. In other words, rotation of the screw 14 does not result in rotation of the washer nut 16 because the stops 56 retard rotational motion of the washer nut. However, rotation of the screw 14 is operative to vertically reposition the washer nut 16 so that the concave surface 84 of the washer 82 is forced against the underneath convex surface 44 of the flange 32. Eventually, after a predetermined amount of clockwise rotation of the screw 14, the head 110 of the screw 14, the base plate 12, and the washer nut 16 cooperate to create a compression joint that locks the screw in the appropriate angular orientation. This is accomplished by the sandwiching action of the washer 82 and the head 110 to capture the flange 32 therebetween as the washer and head are drawn toward one another by the rotation of the screw 14. Conversely, loosening of the compression joint is accomplished by simply rotating the screw 14 in a counterclockwise direction, thereby discontinuing the compression joint.

Figure 17:
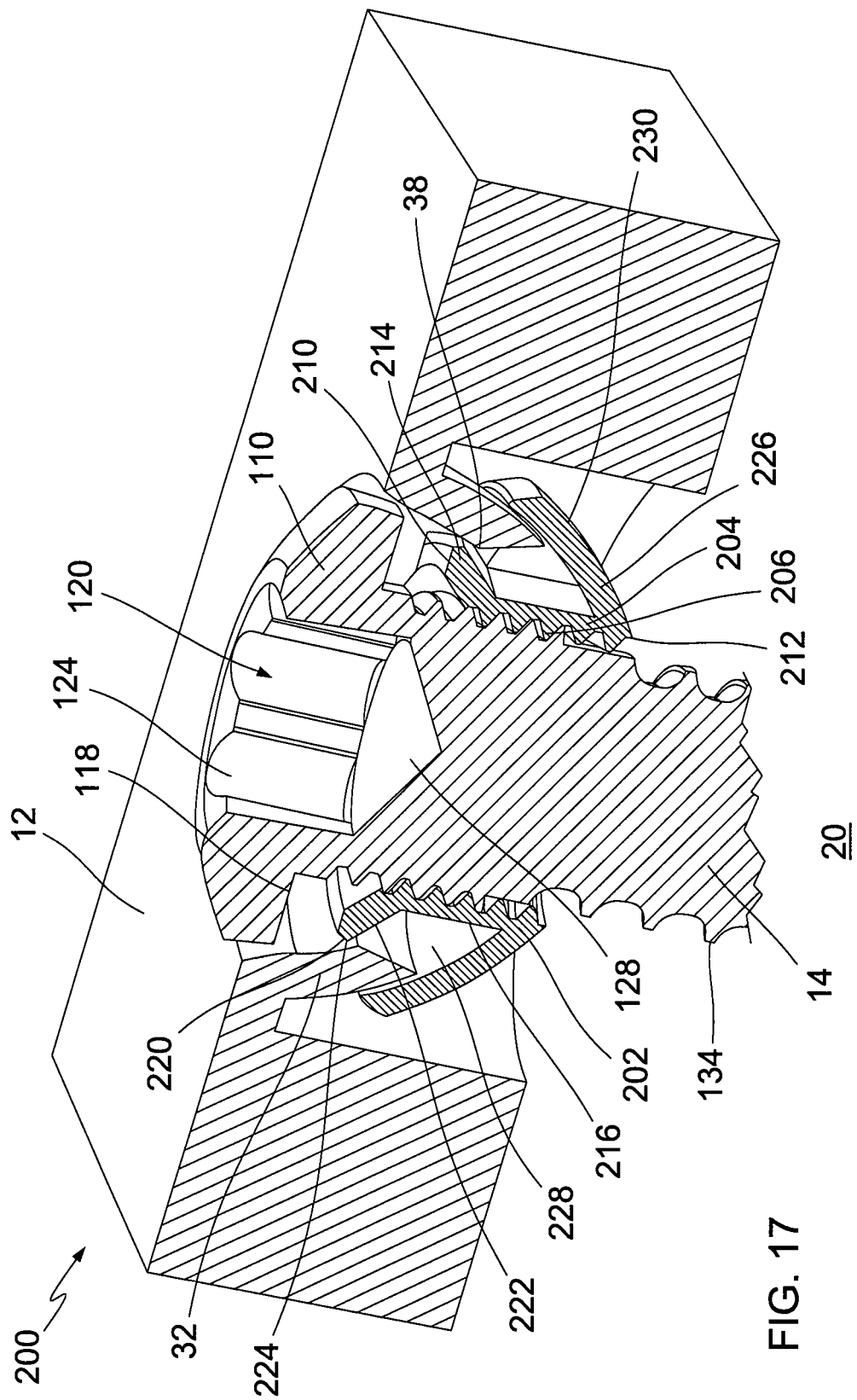
FIG. 17 is an elevated, perspective, cross-sectional view of a second exemplary embodiment of the instant disclosure.
Figure 18:
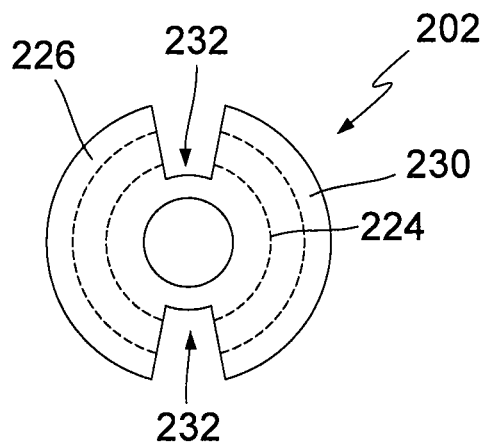
FIG. 18 is a bottom view of a second exemplary threaded nut in accordance with the instant disclosure.
Figure 19:
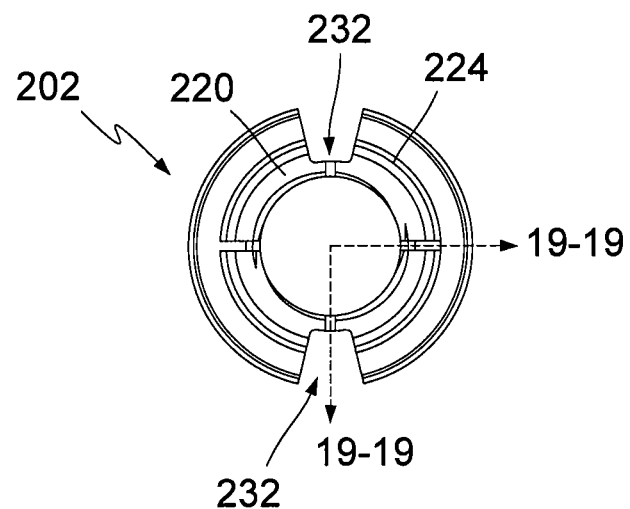
FIG. 19 is a top view of the exemplary threaded nut of FIG. 18.
Figure 20:
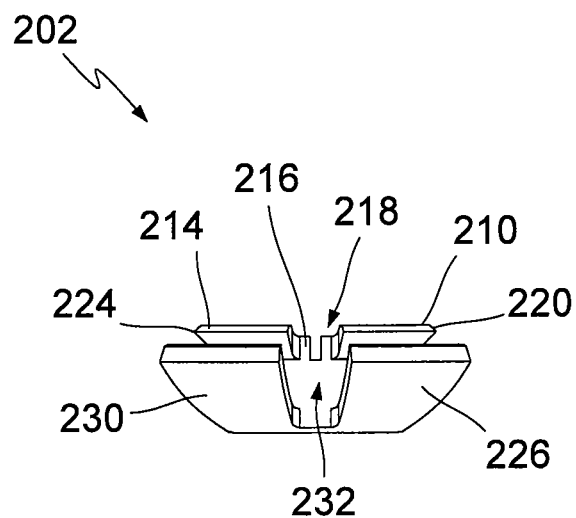
FIG. 20 is a profile view of the exemplary threaded nut of FIG. 18.
Figure 21:
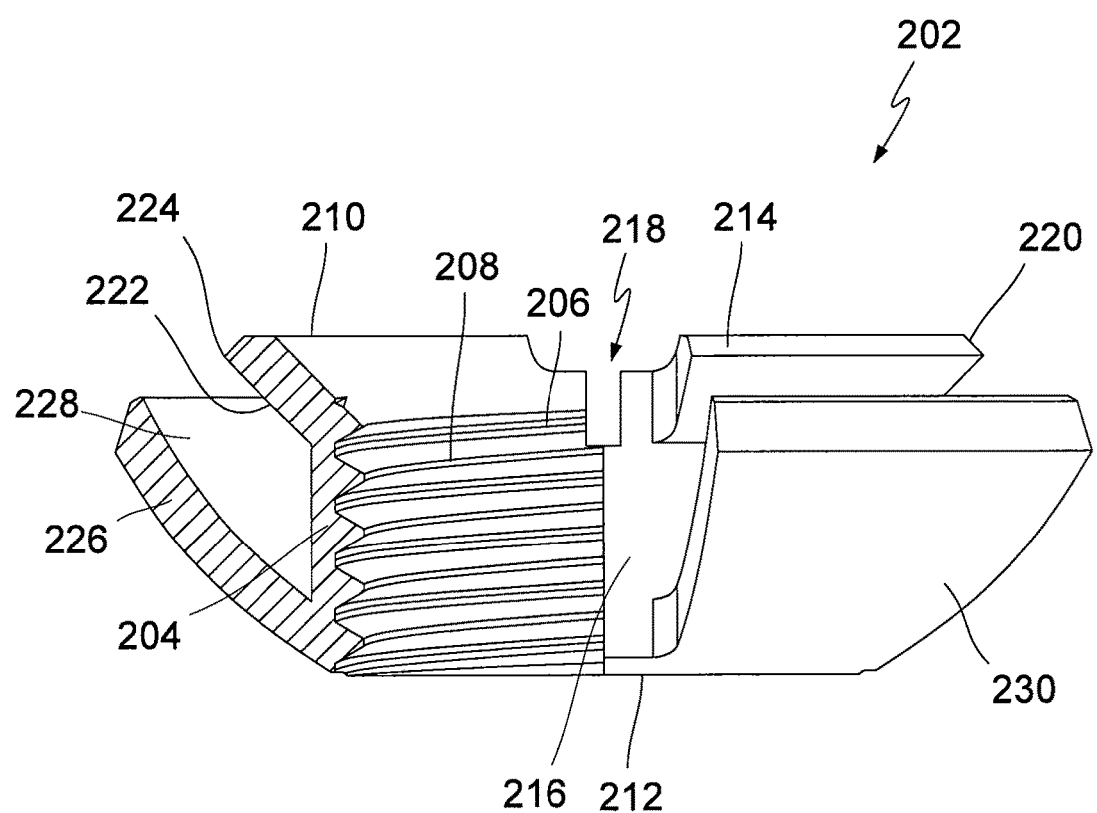
FIG. 21 is a cross-sectional view of an exemplary threaded nut of FIG. 19 taken along lines 19-19.

Referencing FIG. 17, a second exemplary variable angle locking screw assembly 200 comprises the same base plate 12 and screw 14 from the first exemplary embodiment, but uses a different washer nut 202 and does not include a retention ring 18. As with the first exemplary embodiment 10, the components of this second exemplary embodiment 200 cooperate to retain the screw 14 at one of a multitude of predetermined angles with respect to the base plate 12 when the screw is mounted to a biologic substrate 20, such as human bone, and when the screw 14 tightened with respect to the other components of the variable angle locking screw assembly 10.

Referring to FIGS. 18-21, the washer nut 202 includes a hollow cylinder 204 having internal threads 206 formed into or extending from an interior surface 208 of the cylinder. As will be discussed in more detail below, these threads 206 are adapted to interface with threads formed into or extending from the screw 14. The cylinder 204 also includes an upper end 210, opposite a lower end 212, having a discontinuous collar 214 that extends radially out from an exterior surface 216 of the cylinder. In this exemplary embodiment, the collar 214 includes two circumferential sections, with each section being equidistantly spaced and extending approximately 160 degrees around the cylinder 204, thereby leaving two gaps 218 between the collar sections. The collar 214 includes an upper sloped surface 220 and a second lower sloped surface 222 that converge at a point 224, with the point being that portion of the collar 214 that is the farthest radially from the center of the cylinder 204. The lower sloped surface 222 intersects the generally smooth, arcuate exterior surface 216 of the cylinder 204.

The lower end 212 of the hollow cylinder 204 includes a discontinuous dome-shaped washer 226 arcuately extending radially outward and upward from the cylinder 204 and vertically toward the upper end 210. The washer 226 includes opposed concave and convex surfaces 228, 230, where the concave surface 228 generally faces the collar 214. In this exemplary embodiment, the washer 226 includes two circumferential sections, with each section being equidistantly spaced and extending approximately 160 degrees around the cylinder 204, thereby leaving two spaces 232 between the washer sections. Both gaps 218 between the collar 214 sections and the spaces 232 between the washer 226 sections are radially aligned, where the spaces 232 are adapted to selectively receive the stops 56 (see FIGS. 3 and 4) to inhibit rotation of the washer nut 202 with respect to the base plate 12.

Figure 22:
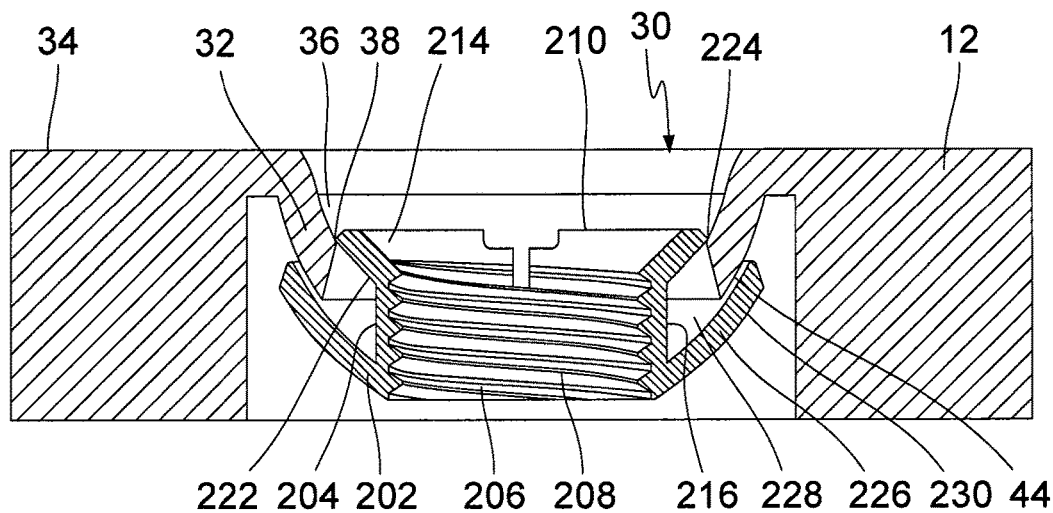
FIG. 22 is a cross-sectional view of the second exemplary embodiment of FIG. 17, with the washer nut relaxed and without the screw.
Figure 23:
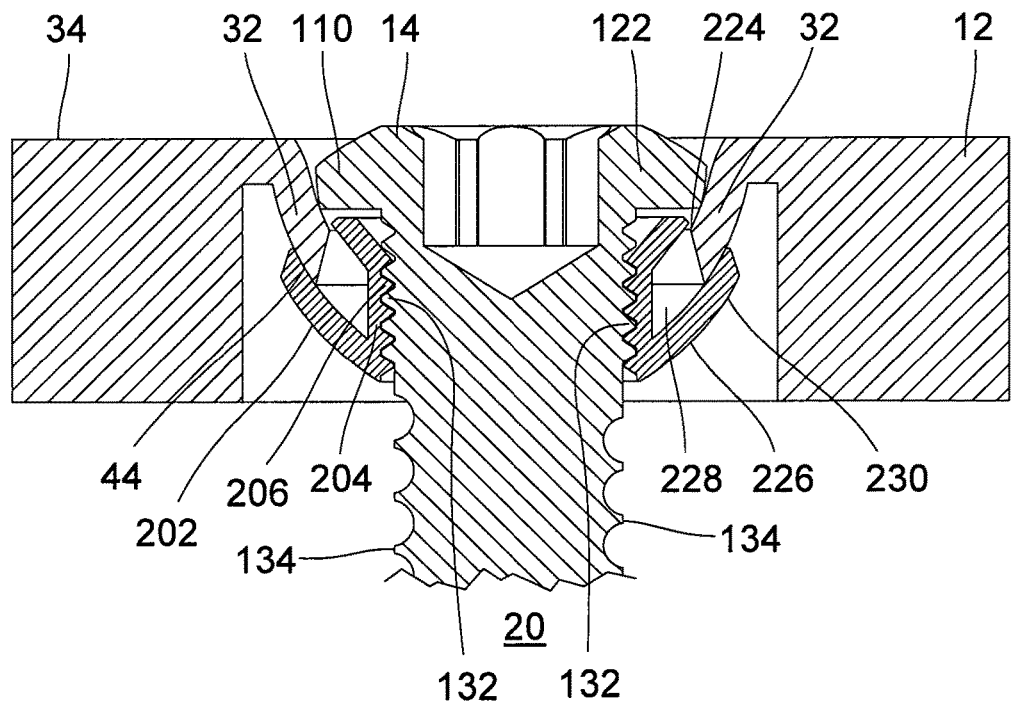
FIG. 23 is a cross-sectional view of the second exemplary embodiment of FIG. 17, with the washer nut (not relaxed) and screw sandwiching the flange.

Referencing FIGS. 17, 22, and 23, the second exemplary variable angle locking screw assembly 200 may also be utilized to secure the biologic substrate 20, such as human bone, in a constant position for proper healing. As with the first exemplary locking screw assembly 10, the second locking screw assembly 200 installation procedure may include drilling a hole into the substrate 20 at a desired angular orientation, where the hole has a diameter less than the diameter of the second set of threads 134 on the opposite end 138 of the screw 14.

In this exemplary embodiment, the washer nut 202 is already mounted to the base plate 12. When the washer nut 202 is mounted to the base plate 12, the default position (presuming the top surface 34 of the base plate 12 is oriented upward) of the washer nut includes the lower sloped surface 222 of the collar 214 contacting the upper surface 36 of the flange 32 (see FIG. 22). Because the outside diameter of the collar 214, measured at the point 224, is greater than the diameter of the through opening 30 measured at the leading edge 38, the collar cannot pass through the through opening. Likewise, because the diameter of the washer 226, measured at its outermost tip, is larger than the diameter of the through opening 30 measured at the leading edge 38, the washer cannot pass through the through opening. In addition, a portion of the hollow cylinder 204 occupies the through opening 30 proximate the leading edge 38 of the flange 32.

After the washer nut 202 is mounted to the base plate 12, a surgeon may then insert a drill bit (not shown) into the through hole 30 and into an opening defined by the hollow cylinder 204 to contact the biologic substrate 20, such as human bone. At this time, the surgeon controls the drill bit to create a hole within the substrate 20 that will ultimately receive the screw 14 in order to mount the base plate 12 to the substrate 20. After the drill bit has completed boring the hole within the substrate 20, the drill bit is withdrawn from the substrate 20, from the through hole 30, and from the hollow cylinder 204.

After removing the drill bit, the screw 14 may be inserted into the through hole 30 and into the hollow cylinder 204 at a desired angular orientation (up to approximately 15 degrees or greater from axial alignment with the through hole 30), with the opposite end 138 of the shaft 112 being inserted first. Specifically, the opposite end 138 of the shaft 112 and the second set of threads 134 are sized to pass into the hollow cylinder 204 without engaging the threads 206 on the interior surface 208 of the cylinder. As the shaft 112 of the screw 14 continues to be inserted and travel through the through hole 30 and into and beyond the hollow cylinder 204, ultimately the head end 122 of the shaft reaches the hollow cylinder 204 at approximately the same time as the conical projection 136 at the opposite end 138 of the screw 14 reaches the previously drilled hole in the substrate 20.

After the screw 14 has been angularly oriented and aligned with the previously drilled hole within the biologic substrate 20, the screw 14 may be tightened and in so doing, retain the angular position of the screw. This may be accomplished rotating the screw 14 in a clockwise direction so that the threads 132 at the head end 122 engage the threads 206 on the interior surface 208 of the cylinder 204 to couple the screw 14 to the washer nut 202. At the same time, clockwise rotation of the screw 14 is operative to engage the second set of threads 134 with the biologic substrate 20. As the screw 14 is rotated in a clockwise direction (between 1-3 turns, for example), the stops 56 of the base plate 12 (see FIGS. 3 and 4) continue to be received within the spaces 232 of the washer 226 to inhibit rotation of the washer nut 202 with respect to the base plate 12. In other words, rotation of the screw 14 does not result in rotation of the washer nut 202 because the stops 56 retard rotational motion of the washer nut. However, rotation of the screw 14 is operative to vertically reposition the washer nut 202 so that the concave surface 228 of the washer 226 is forced against the underneath convex surface 44 of the flange 32. Eventually, after a predetermined amount of clockwise rotation of the screw 14, the head 110 of the screw 14, the base plate 12, and the washer nut 202 cooperate to create a compression joint that locks the screw in the appropriate angular orientation (see FIG. 23). This is accomplished by the sandwiching action of the washer 226 and the head 110 to capture the flange 32 therebetween as the washer and head are drawn toward one another by the rotation of the screw 14. Conversely, loosening of the compression joint is accomplished by simply rotating the screw 14 in a counterclockwise direction, thereby discontinuing the compression joint (see FIG. 17).

Figure 24:
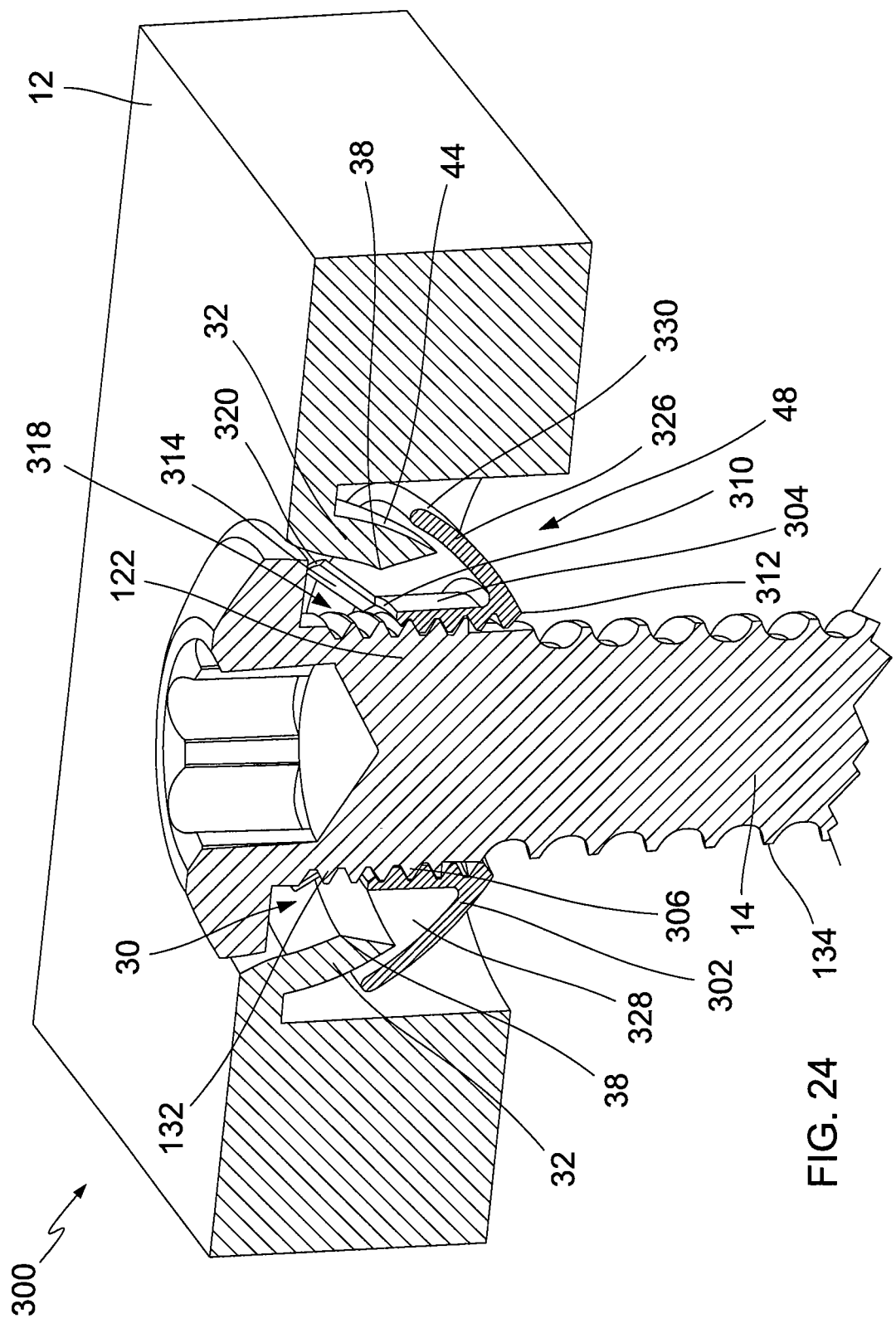
FIG. 24 is a cross-sectional view of a third exemplary embodiment of the instant disclosure.

Referencing FIG. 24, a third exemplary variable angle locking screw assembly 300 comprises the same base plate 12 and screw 14 from the first exemplary embodiment, but uses a different washer nut 302 and does not include a retention ring 18. As with the first exemplary embodiment 10, the components of this third exemplary embodiment 300 cooperate to retain the screw 14 at one of a multitude of predetermined angles with respect to the base plate 12 when the screw is mounted to a biologic substrate 20, such as human bone, and when the screw 14 is tightened with respect to the other components of the variable angle locking screw assembly 300.

Figure 25:
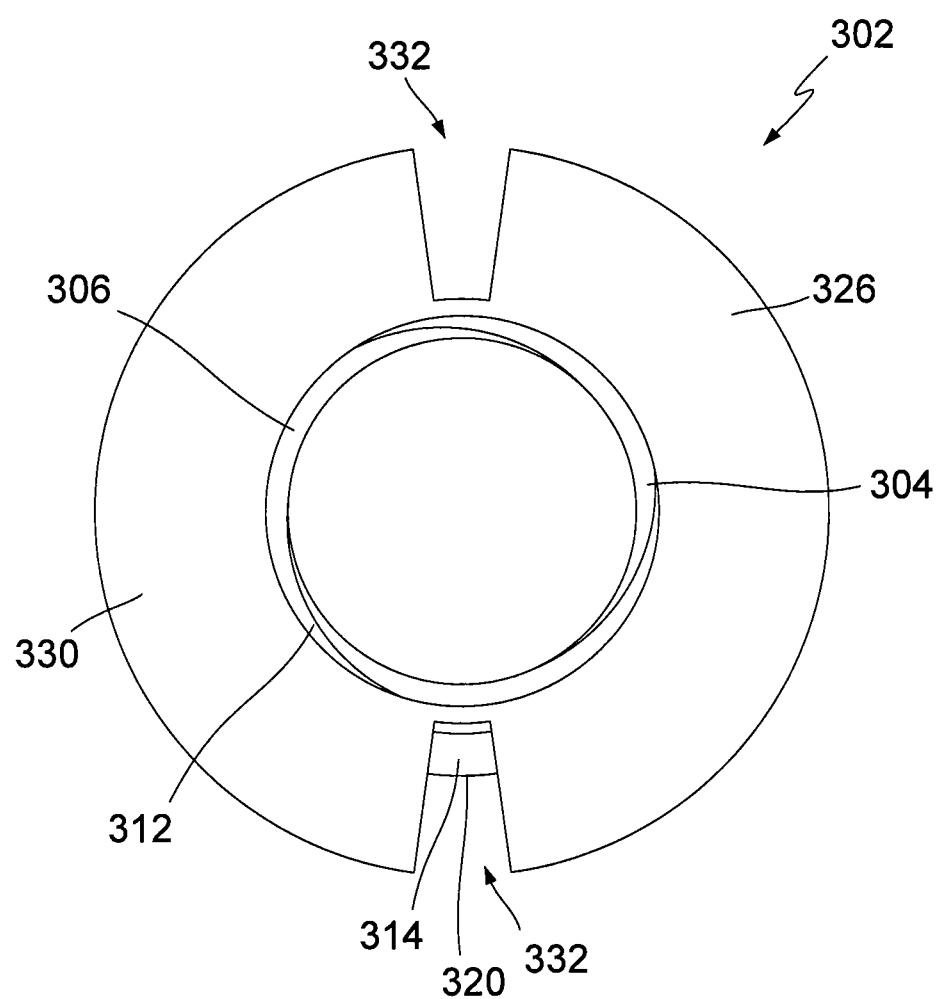
FIG. 25 is a bottom view of a third exemplary threaded nut in accordance with the instant disclosure.
Figure 26:
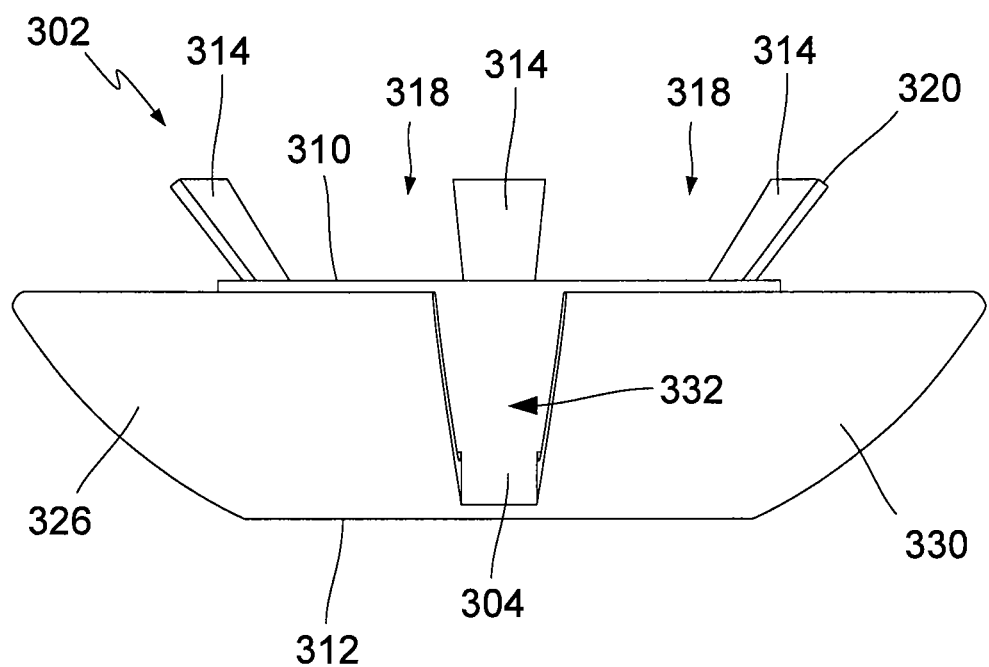
FIG. 26 is a profile view of the exemplary threaded nut of FIG. 25.
Figure 27:
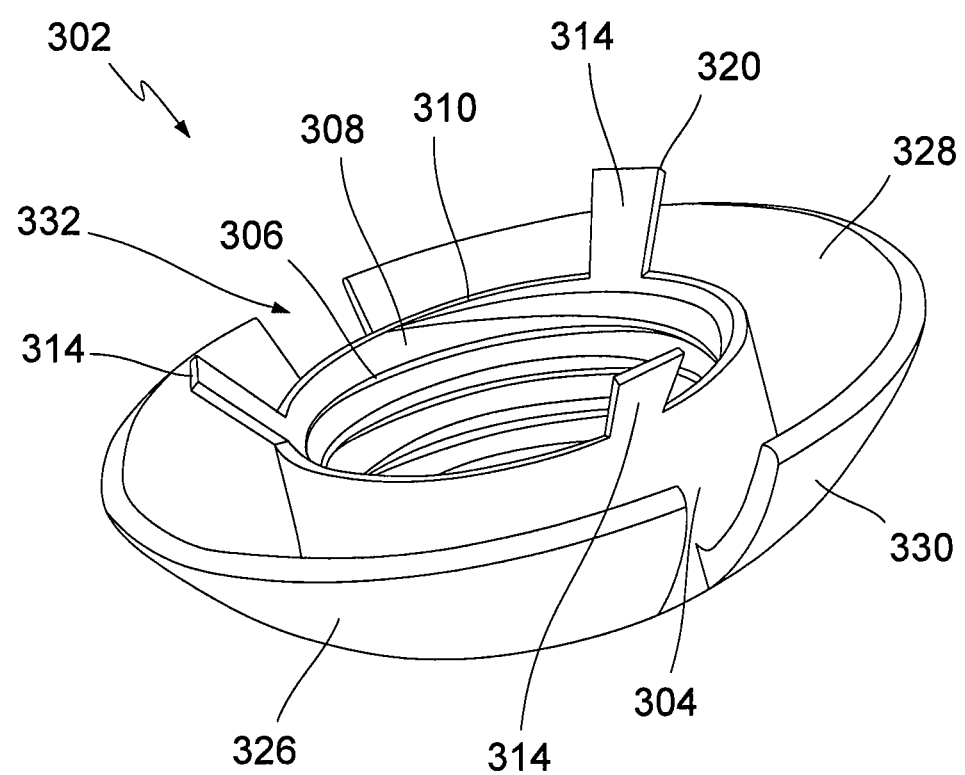
FIG. 27 is a top, perspective view of the exemplary threaded nut of FIG. 25.

Referring to FIGS. 25-27, the washer nut 302 includes a hollow cylinder 304 having internal threads 306 formed into or extending from an interior surface 308 of the cylinder. As will be discussed in more detail below, these threads 306 are adapted to interface with threads formed into or extending from the screw 14. The cylinder 304 also includes an upper end 310, opposite a lower end 312, having a plurality of trapezoidal projections 314 that extend radially out and vertically up from the upper end 310. In this exemplary embodiment, there are three trapezoidal projections 314 being equidistantly spaced and circumferentially distributed about the circumference of the upper end 310, thereby leaving three gaps 318 between the trapezoidal projections. The outer end 320 of each trapezoidal projection 314 cooperates to define an annular perimeter having a diameter that is greater than the diameter of the through hole 30 measured at the leading edge 38 of the flange 32.

The lower end 312 of the hollow cylinder 304 includes a discontinuous dome-shaped washer 326 arcuately extending radially outward from the cylinder 304 and vertically up toward the upper end 310. The washer 326 includes opposed concave and convex surfaces 328, 330, where the concave surface 328 generally faces the trapezoidal projections 314. In this exemplary embodiment, the washer 326 includes two circumferential sections, with each section being equidistantly spaced and extending approximately 160 degrees around the cylinder 304, thereby leaving two spaces 332 between the washer sections. The spaces 332 between the washer 326 sections are adapted to selectively receive the stops 56 (see FIGS. 3 and 4) of the base plate 12 to inhibit rotation of the washer nut 302 with respect to the base plate 12.

Figure 28:
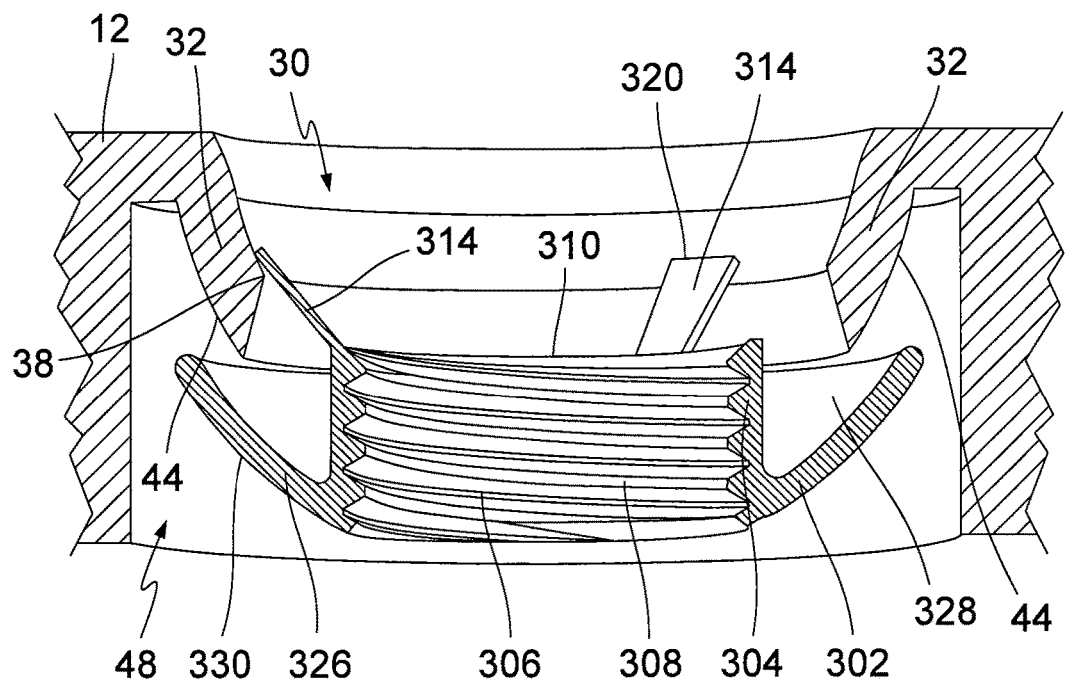
FIG. 28 is a cross-sectional view of the third exemplary embodiment of FIG. 24, with the washer nut relaxed and without the screw.
Figure 29:
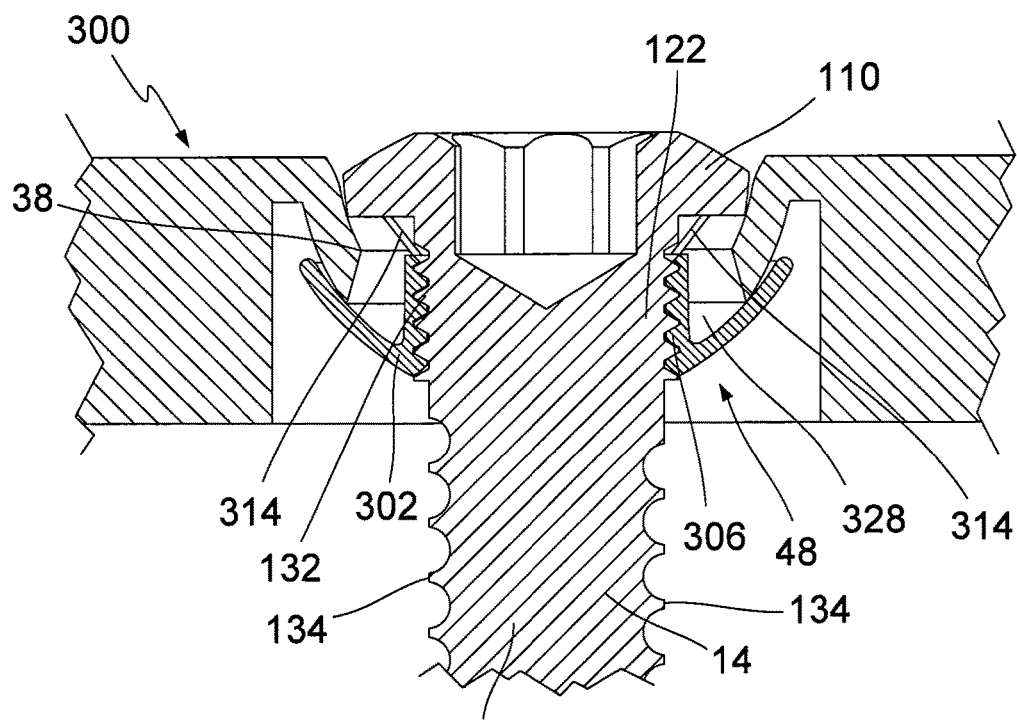
FIG. 29 is a cross-sectional view of the third exemplary embodiment of FIG. 24, with the washer nut (not relaxed) and screw sandwiching the flange.

Referencing FIGS. 24, 28, and 29, the third exemplary variable angle locking screw assembly 300 may also be utilized to secure the biologic substrate 20, such as human bone, in a constant position for proper healing. As with the first exemplary locking screw assembly 10, the third locking screw assembly 300 installation procedure may include drilling a hole into the substrate 20 at the desired angular orientation, where the hole has a diameter less than the diameter of the second set of threads 134 on the opposite end 138 of the screw 14.

By way of example, the washer nut 302 is oriented so that the upper end 310 of the cylinder 304 is inserted initially into the cavity 48, followed by the washer 326 end of the washer nut 302. The cylinder 304 is moved further into the cavity 48 so that the trapezoidal projections 314 are immediately below leading edge 38 of the flange 32. In other words, the perimeter defined by the leading edge 38 is generally coaxial with the perimeter defined by the far ends 320 of the trapezoidal projections 314. The trapezoidal projections 314 are deformed radially inward to reduce the diameter of the perimeter defined by the far ends 320 of the trapezoidal projections 314 until the diameter is small enough pass by the leading edge 38 of the flange 32, thereby allowing insertion of the near end 310 of the cylinder 304 further into the through opening 30. After the deformed trapezoidal projections 314 clear the through opening 30 at the leading edge 38 of the flange 32, the trapezoidal projection are allowed to return to a default position. This default position includes radially deforming the trapezoidal projections 314 outward to increase the diameter of the perimeter defined by the far ends 320 of the trapezoidal projections 314 until the diameter is large enough to inhibit removal of the near end 310 of the cylinder 304 beyond the through opening 30. This procedure effectively mounts the washer nut 302 to the base plate 12.

After the washer nut 302 is mounted to the base plate 12, a surgeon may then insert a drill bit (not shown) into the through hole 30 and into the through hole defined by the hollow cylinder 304 to contact the biologic substrate 20, such as human bone. At this time, the surgeon controls the drill bit to create a hole within the substrate 20 that will ultimately receive the screw 14 in order to mount the base plate 12 to the substrate 20. After the drill bit has completed boring the hole within the substrate 20, the drill bit is withdrawn from the substrate 20, from the through hole 30, and from the hollow cylinder 304.

After removing the drill bit, the screw 14 may be inserted into the through hole 30 and into the hollow cylinder 304 at a desired angular orientation (up to approximately 15 degrees or greater from axial alignment with the through hole 30), with the opposite end 138 of the shaft 112 being inserted first. Specifically, the opposite end 138 of the shaft 112 and the second set of threads 134 are sized to pass into the hollow cylinder 304 without engaging the threads 306 on the interior surface 308 of the cylinder. As the shaft 112 of the screw 14 continues to be inserted and travel through the through hole 30 and into and beyond the hollow cylinder 304, ultimately the head end 122 of the shaft reaches the hollow cylinder 304 at approximately the same time as the screw 14 (specifically the conical projection 136 at the opposite end 138 of the screw 14) reaches the hole in the substrate 20.

After the screw 14 has been angularly oriented and aligned with the previously drilled hole into the biologic substrate 20, the screw 14 may be tightened and in so doing, retain the angular position of the screw. This may be accomplished by rotating the screw 14 in a clockwise direction so that the threads 132 at the head end 122 of the shaft 112 engage the threads 306 on the interior of the cylinder 304 to couple the screw 14 to the washer nut 302. At the same time, clockwise rotation of the screw 14 is operative to engage the second set of threads 134 with the biologic substrate 20. As the screw 14 is rotated in a clockwise direction (between 1-3 turns, for example), the stops 56 (see FIGS. 3 and 4) of the base plate 12 continue to be received within the two spaces 332 of the washer 326 to inhibit rotation of the washer nut 302 with respect to the base plate 12. In other words, rotation of the screw 14 does not result in rotation of the washer nut 302 because the stops 56 retard rotational motion of the washer nut. However, rotation of the screw 14 is operative to vertically reposition the washer nut 302 so that the concave surface 328 of the washer 326 is forced against the underneath convex surface 44 of the flange 32. Eventually, after a predetermined amount of clockwise rotation of the screw 14, the head 110 of the screw 14, the base plate 12, and the washer nut 302 cooperate to create a compression joint that locks the screw in the appropriate angular orientation (see FIG. 29). This is accomplished by the sandwiching action of the washer 326 and the head 110 to capture the flange 32 therebetween as the washer and head are drawn toward one another by the rotation of the screw 14. Conversely, loosening of the compression joint is accomplished by simply rotating the screw 14 in a counterclockwise direction, thereby discontinuing the compression joint (see FIG. 24).

Figure 30:
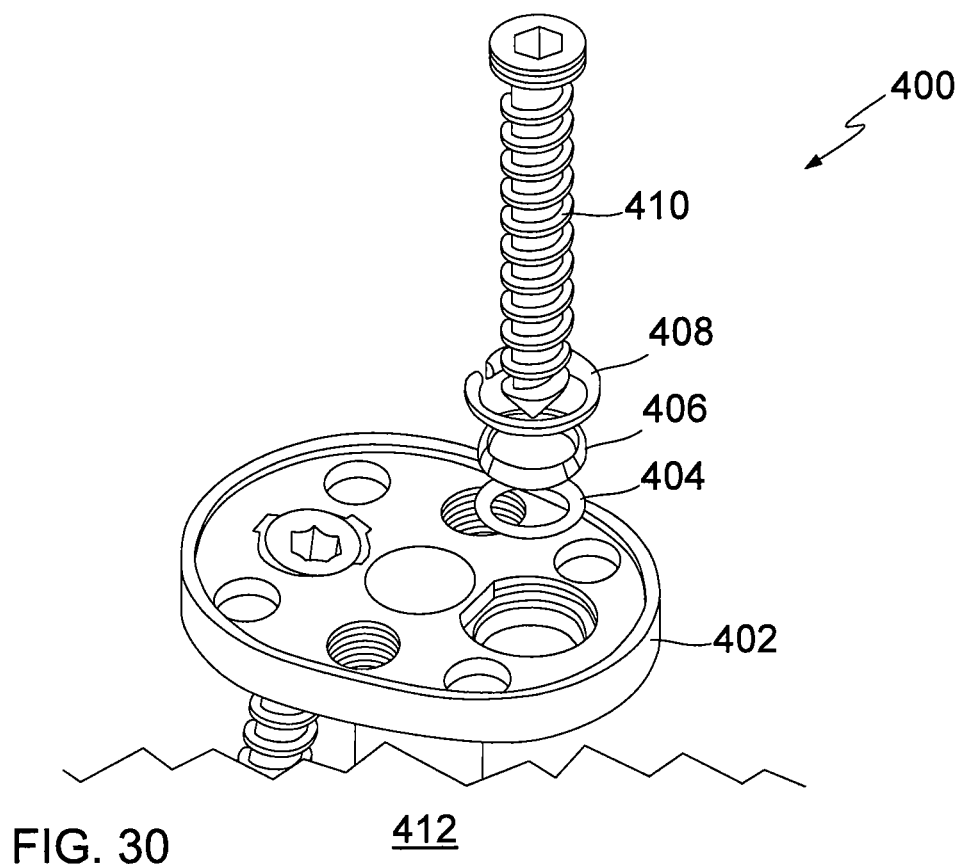
FIG. 30 is an exploded view of a fourth exemplary embodiment of the instant disclosure.
Figure 31:
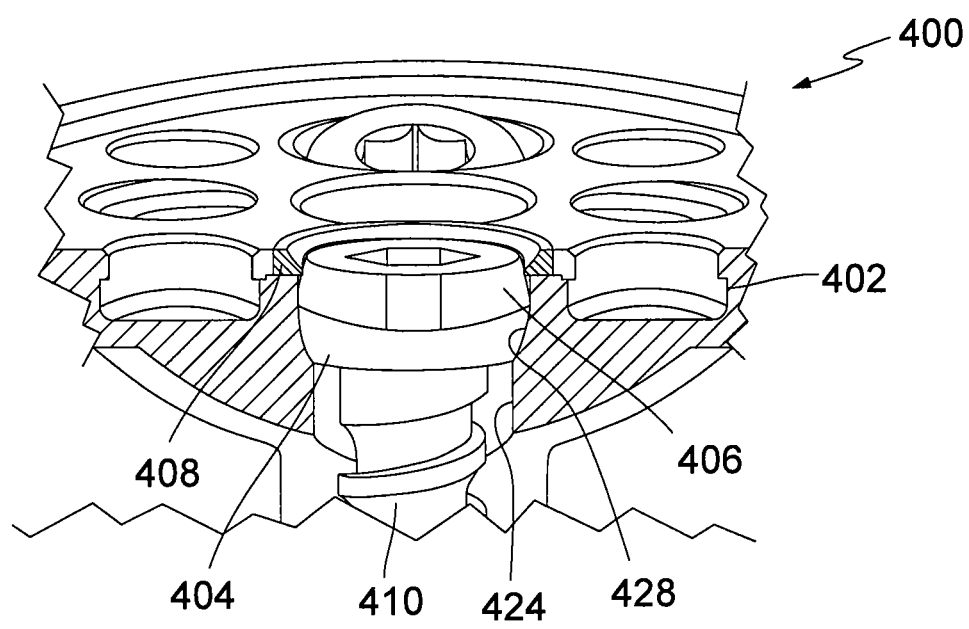
FIG. 31 is an isolated, elevated perspective, cross-sectional profile view of the exemplary embodiment of FIG. 30.
Figure 32:
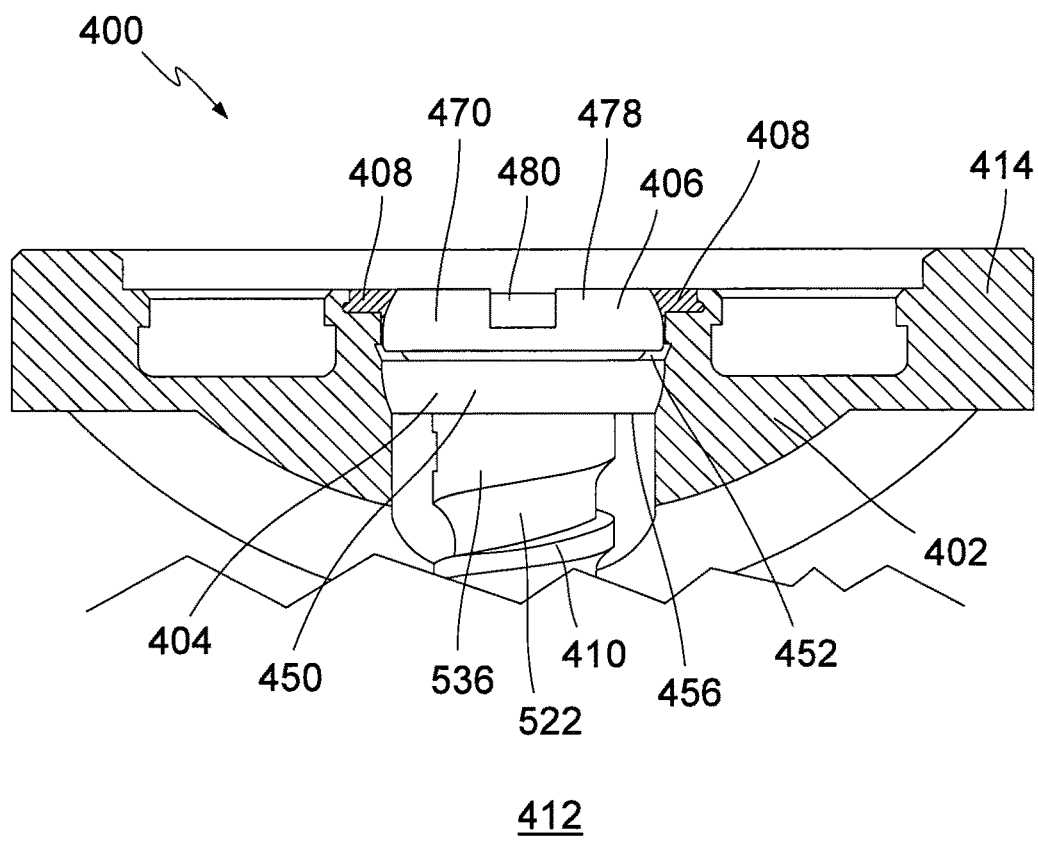
FIG. 32 is an isolated, cross-sectional profile view of the exemplary embodiment of FIG. 30.
Figure 33:
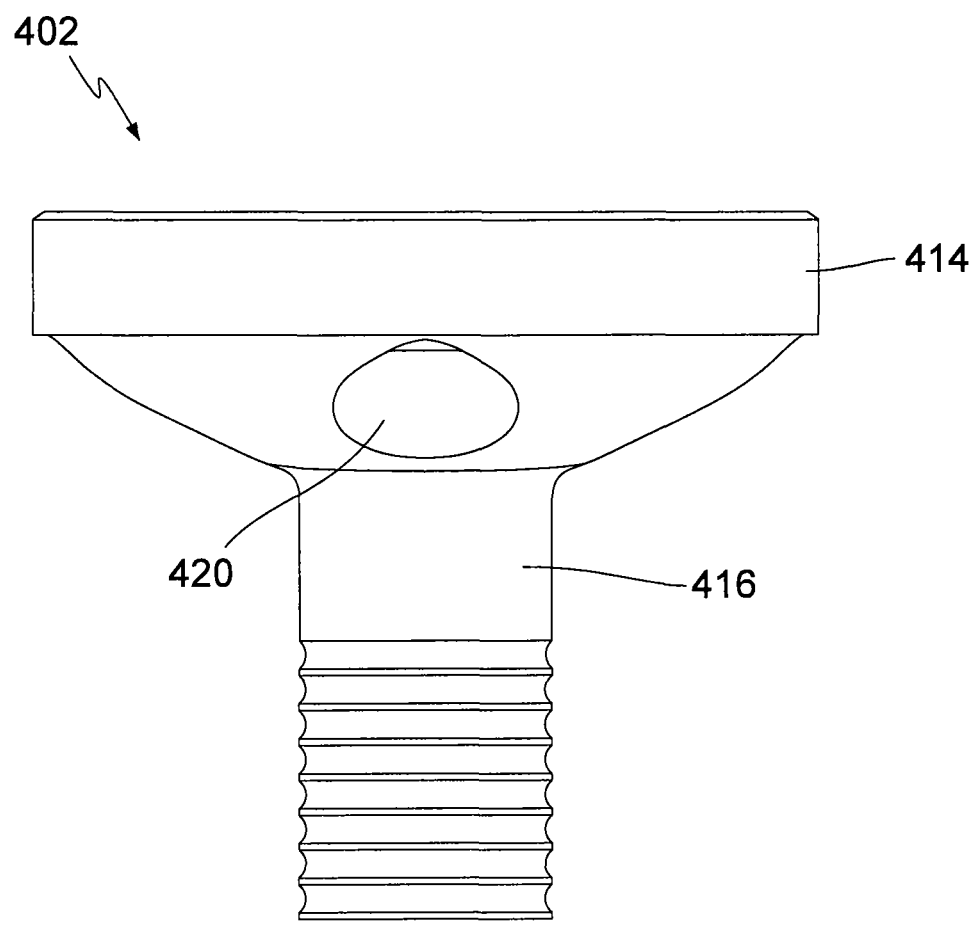
FIG. 33 is a profile view of an exemplary base plate of the embodiment of FIG. 30.
Figure 34:
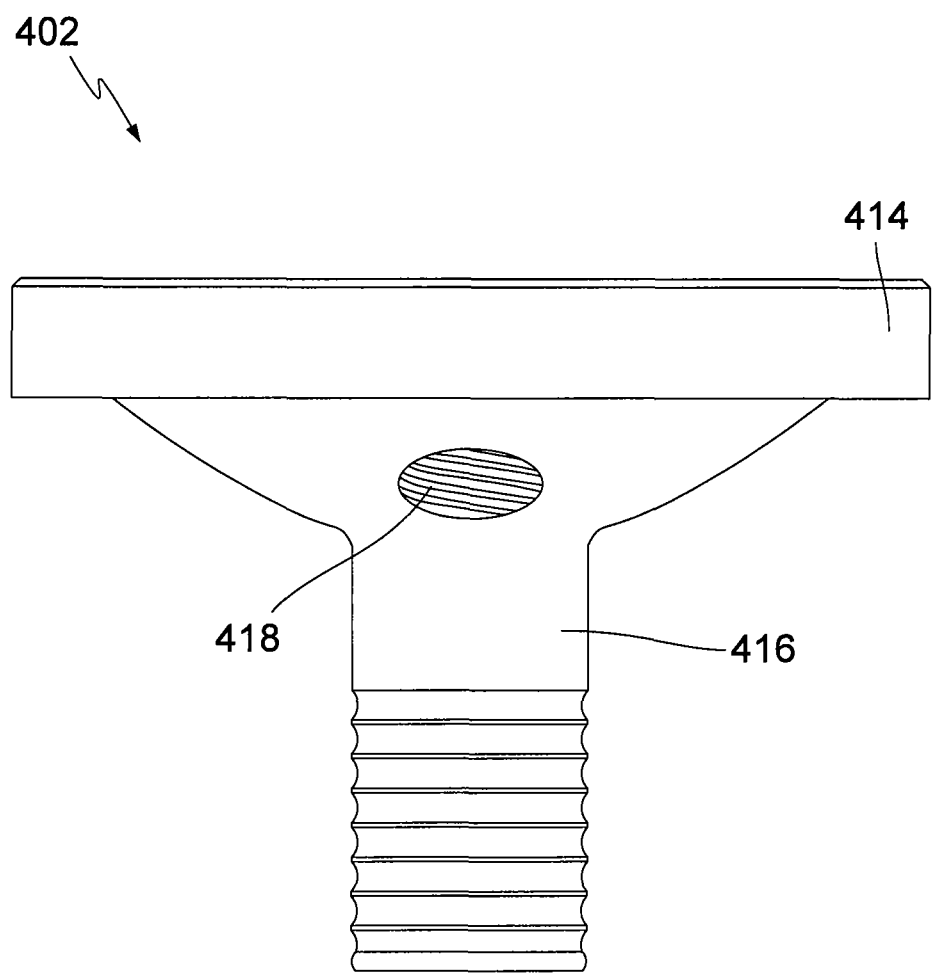
FIG. 34 is a frontal view of an exemplary base plate of the embodiment of FIG. 30.
Figure 35:
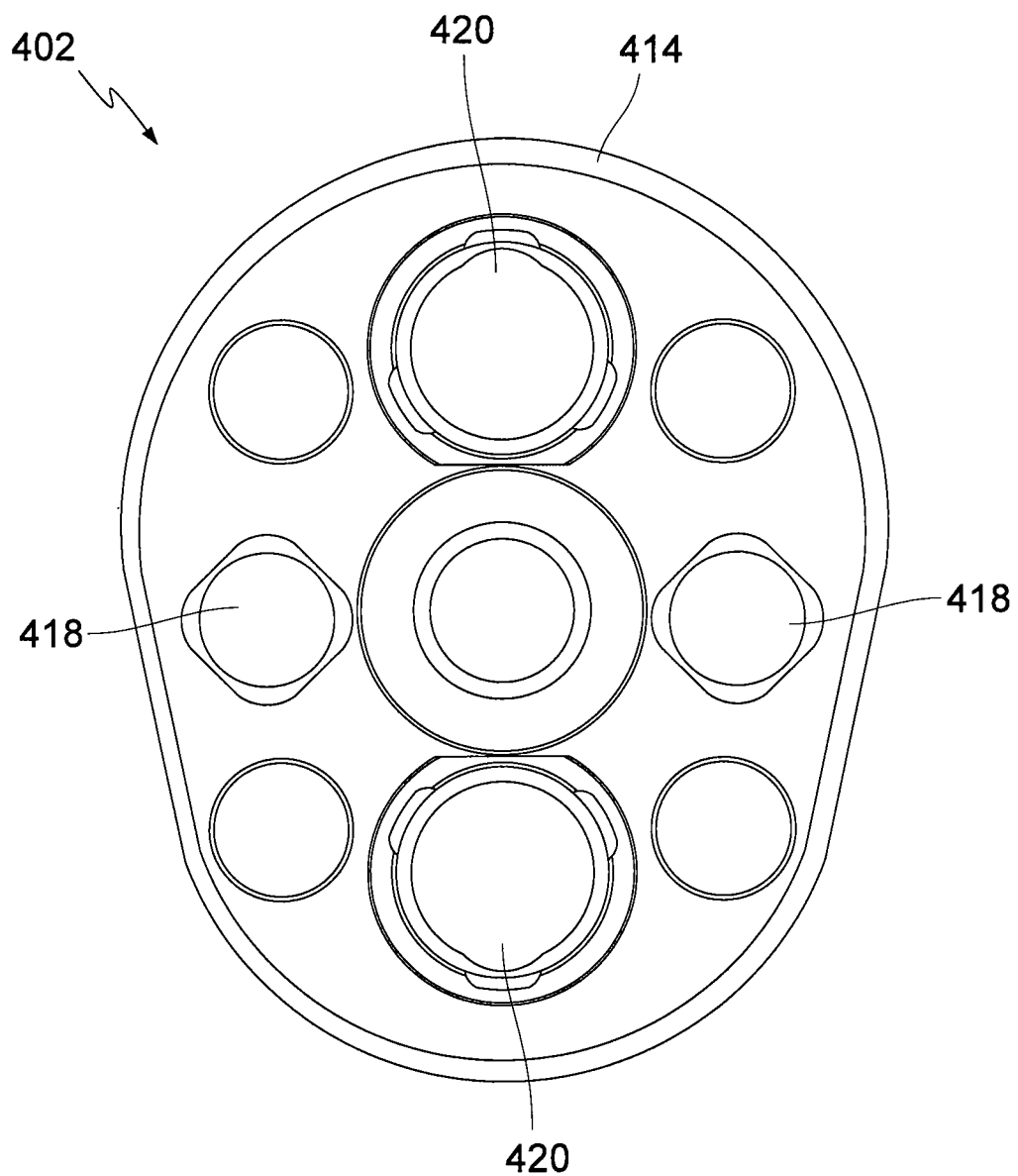
FIG. 35 is a top view of an exemplary base plate of the embodiment of FIG. 30.

Referencing FIGS. 30-32, a fourth exemplary variable angle locking screw assembly 400 comprises a base plate 402, a positioning washer 404, a threaded pressing washer 406, a locking ring 408, and a screw 410. These components cooperate to retain the screw 410 at one of a multitude of predetermined angles with respect to the base plate 402 when the screw is mounted to a biologic substrate 412, such as human bone, as well as when the screw 410 is tightened with respect to the other components of the variable angle locking screw assembly 400.

Referring specifically to FIGS. 32-37, the exemplary base plate 402 includes an upper tray 414 integrally mounted to a threaded stem 416. The upper tray 414 includes a plurality of through holes 418, 420, at least two of which 418 are each adapted to receive a fixed orientation fastener (not shown), while another pair 420 are each adapted to receive a washer 404, a threaded washer 406, a locking ring 408, and a variable angle screw 410.

Figure 36:
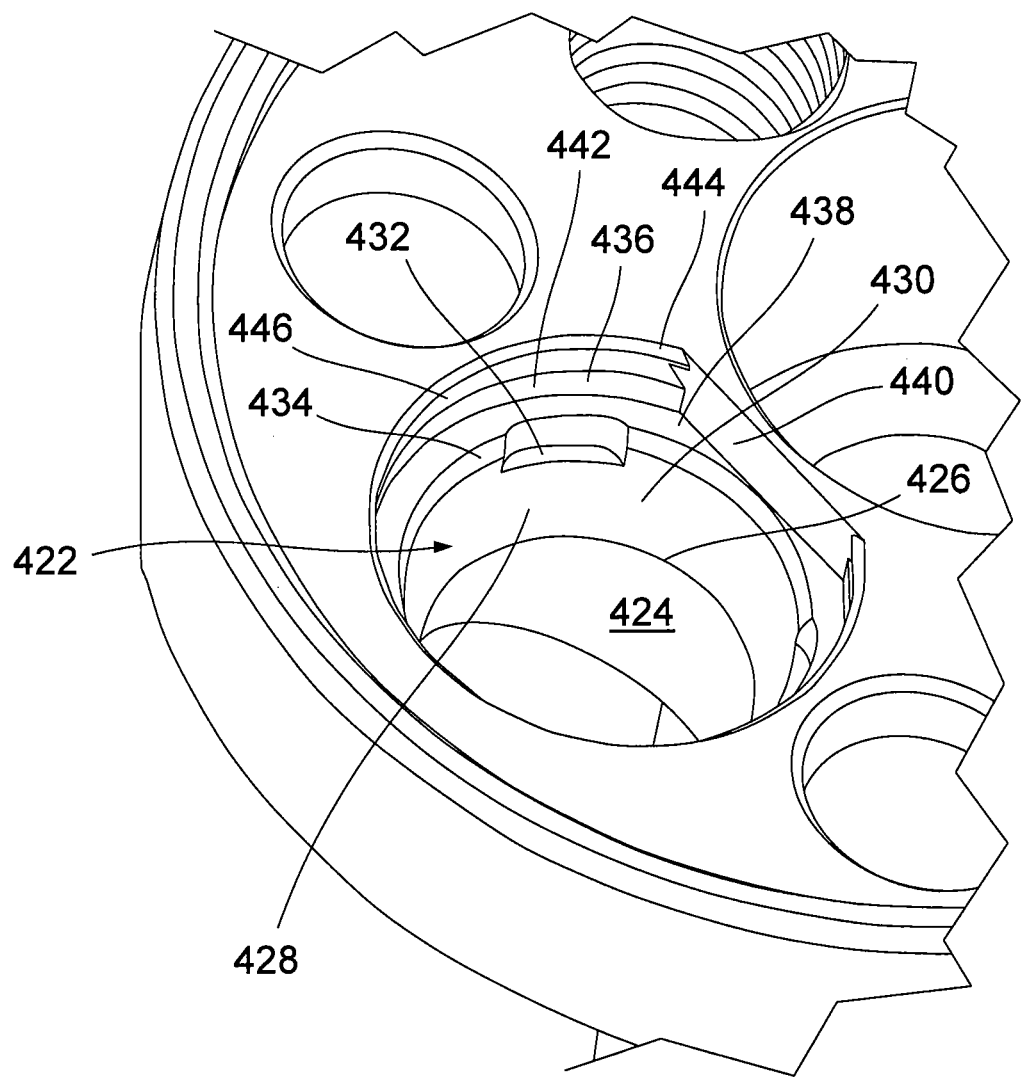
FIG. 36 is an isolated, elevated perspective view of the exemplary base plate of the embodiment of FIG. 30.
Figure 37:
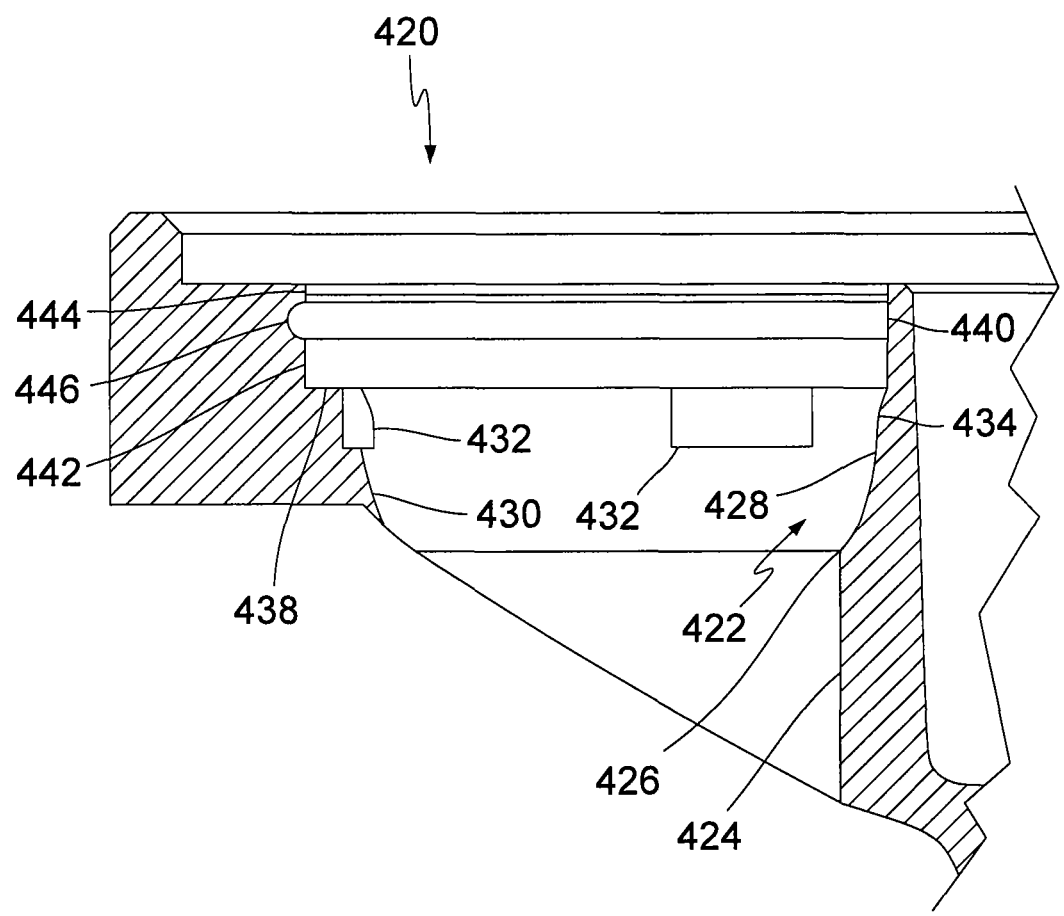
FIG. 37 is an isolated, cross-sectional frontal view of an exemplary base plate of the embodiment of FIG. 30.

Referring specifically to FIGS. 36 and 37, each of the through holes 420 receiving components of the variable angle locking screw assembly 400 are defined by a circumferential wall 422. The circumferential wall 422 actually comprises a series of vertical wall segments that are stacked upon one another and contoured to specifically accommodate the components of the variable angle locking screw assembly 400 in a predetermined order. A first vertical wall segment 424 is located at the bottom of the through hole 420 and comprises a hollow cylindrical tube with a beveled cut. The portion of the first vertical wall segment 424 that is completely circumferentially bounded has a circular cross-section with a substantially constant diameter along its vertical length. A lip 426 differentiates the first wall segment 424 from a second wall segment 428.

The second wall segment 428 also comprises a hollow cylindrical tube that is generally bowl-shaped. Specifically, starting at the lip 426, the second segment 428 exhibits a circular cross-section that is defined by an arcuate wall 430 tapering outward and upward as the vertical distance from the lip increases. A series of cut-outs or notches 432 are formed into the top portion of the arcuate wall 430 and circumferentially distributed therealong. As will be discussed in more detail below, these cutouts 432 receive circumferential projections of the threaded washer 406 to inhibit the washer 406 from rotating. The arcuate wall 430 essentially provides a bowl-shaped contour that transitions into a second arcuate wall 434 at the very top of the second wall segment 428, opposite the lip 426. As with the first arcuate wall 430, the cutouts 432 are also formed into the second arcuate wall 434. But the top of the second arcuate wall 434 signals a significant change in the contour of the circumferential wall 422 to a third vertical wall segment 436.

A horizontal ledge 438 signals the transition from the second vertical wall segment 428 to the third vertical wall segment 436. The ledge 438 is adjacent to the second arcuate wall 434 and is generally circular, but at its ends abuts a vertical, planar wall 440 extending tangentially with respect to the arcuate wall 434. This planar wall 440 also intersects a vertical, circumferential wall 442 that extends vertically from the ledge 438 to a top beveled edge 444 of the through hole 420. A semicircular depression 446 is formed within the circumferential wall 442 in order to receive a portion of the locking ring 408 (see FIGS. 30 and 31) to mount the locking ring to the base plate 402.

Figure 38:
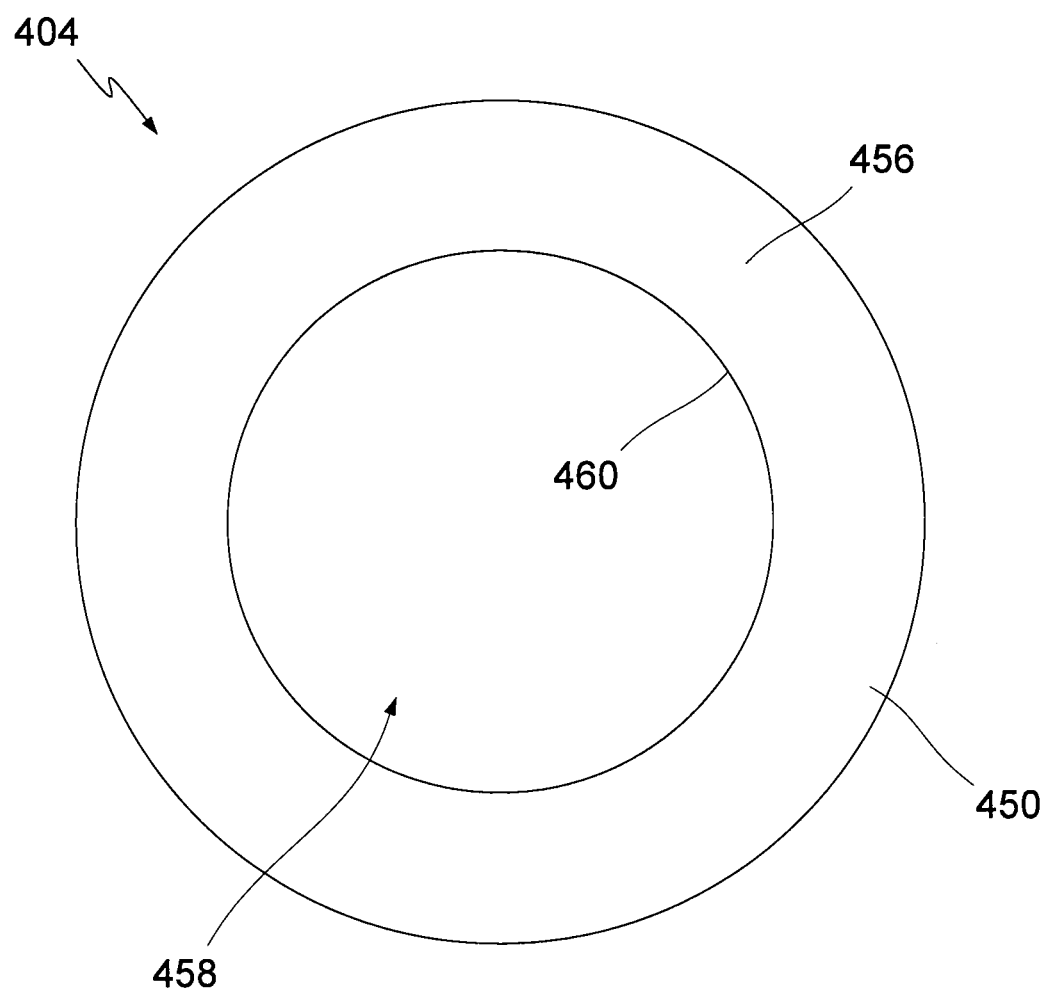
FIG. 38 is a bottom view of an exemplary washer of the embodiment of FIG. 30.
Figure 39:
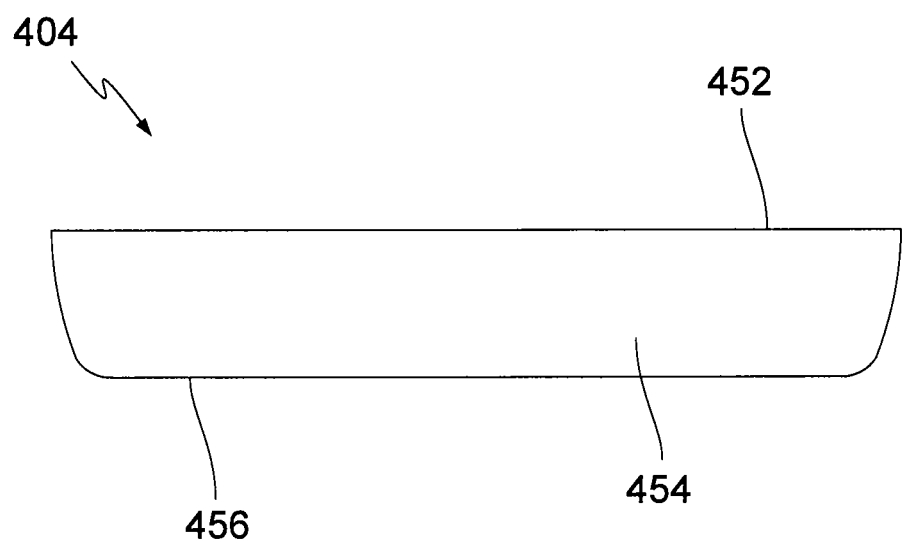
FIG. 39 is a profile view of the exemplary washer of FIG. 38.
Figure 40:
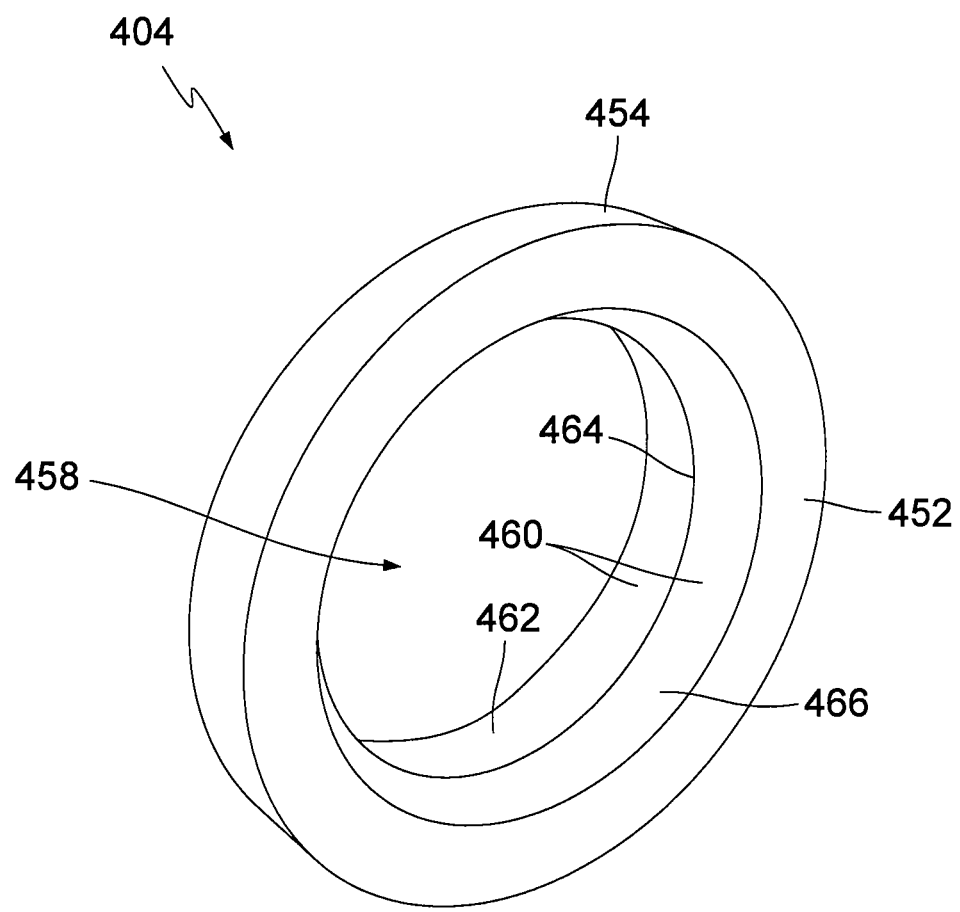
FIG. 40 is a top, perspective view of the exemplary washer of FIG. 38.

Referencing FIGS. 38-40, the positioning washer 404 comprises a generally circular body having a continuous outer wall 450 and a substantially flat, circular top surface 452 that transitions at the outermost perimeter to an arcuate or dome-shaped circumferential surface 454. The circumferential surface 454 tapers inward to decrease the outer diameter of the washer 404 as the distance from the top surface 452 increases. The bottom of the circumferential surface 454 rounds over to seamlessly transition into a substantially flat, circular bottom surface 456. Similar to the top surface 452, the bottom surface 456 partially defines a circular opening 458 that extends through the washer 404. The circular opening 458 is defined by an internal surface 460 that extends between the top and bottom surfaces 452, 456 and is inset with respect to the circumferential surface 454. The internal surface 460 comprises a first wall section 462, adjacent the bottom surface 456, having a substantially constant diameter. A bead 464 interposes the first wall section 462 and a second wall section 466. This second wall section 466 extends upward and includes an arcuate surface operative to gradually increase the diameter of the opening 458 to a maximum diameter adjacent the top surface 452. When assembled, the washer 404 is inserted into the base plate 402 first, followed by the threaded washer 406.

Figure 41:
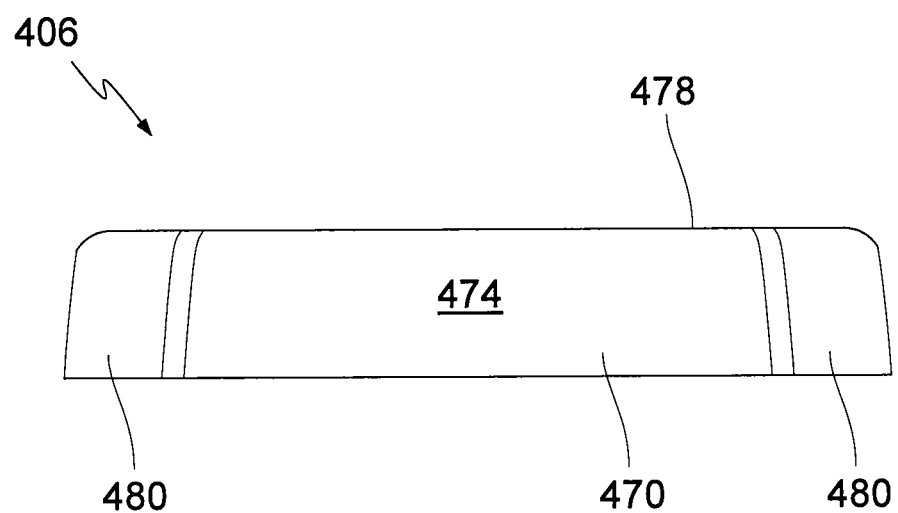
FIG. 41 is a profile view of an exemplary threaded washer of the exemplary base plate of the embodiment of FIG. 30.
Figure 42:
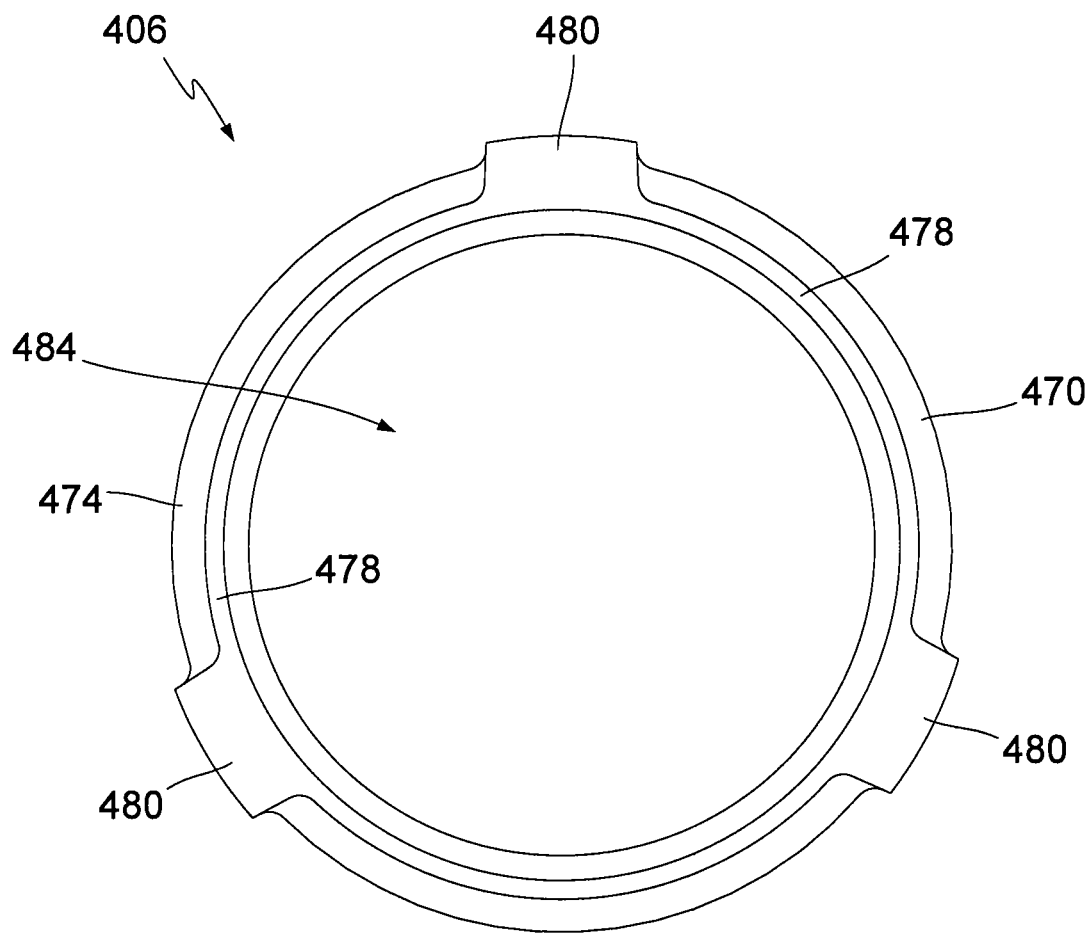
FIG. 42 is a top view of the exemplary threaded washer of FIG. 41.
Figure 43:
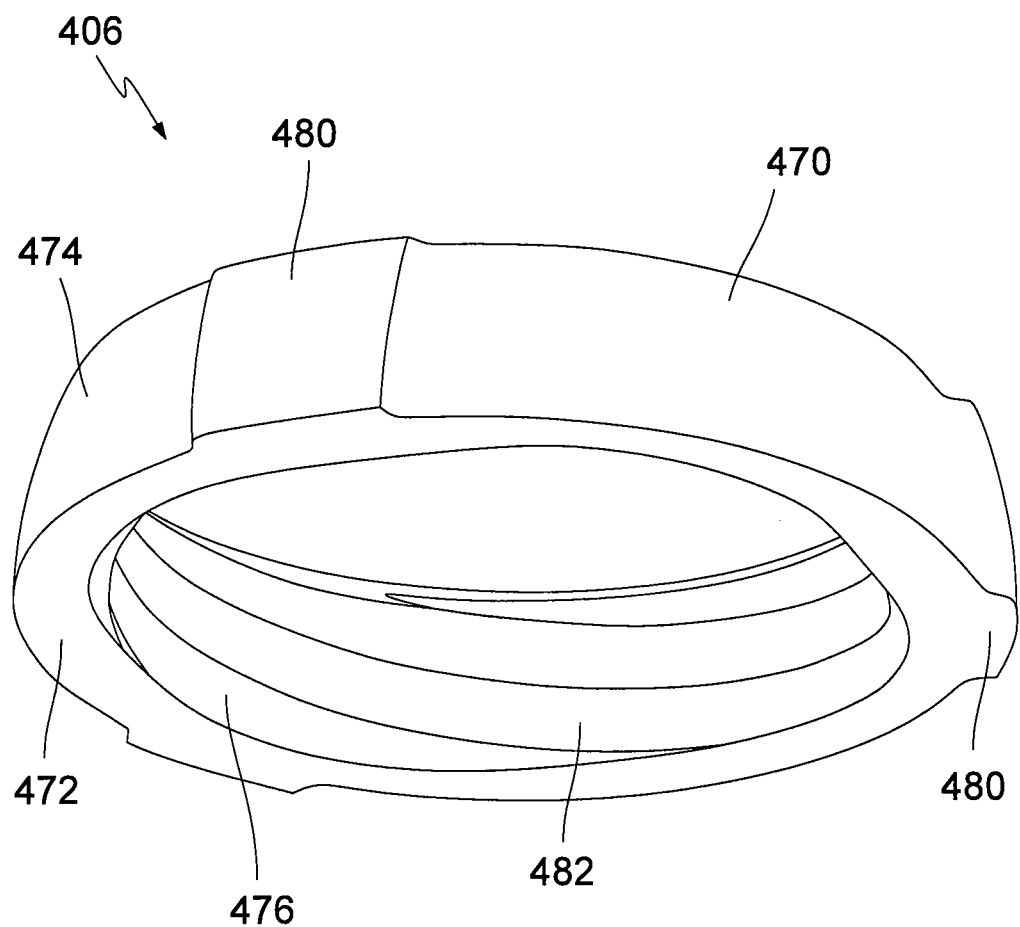
FIG. 43 is a bottom, perspective view of the exemplary threaded washer of FIG. 41.
Figure 44:
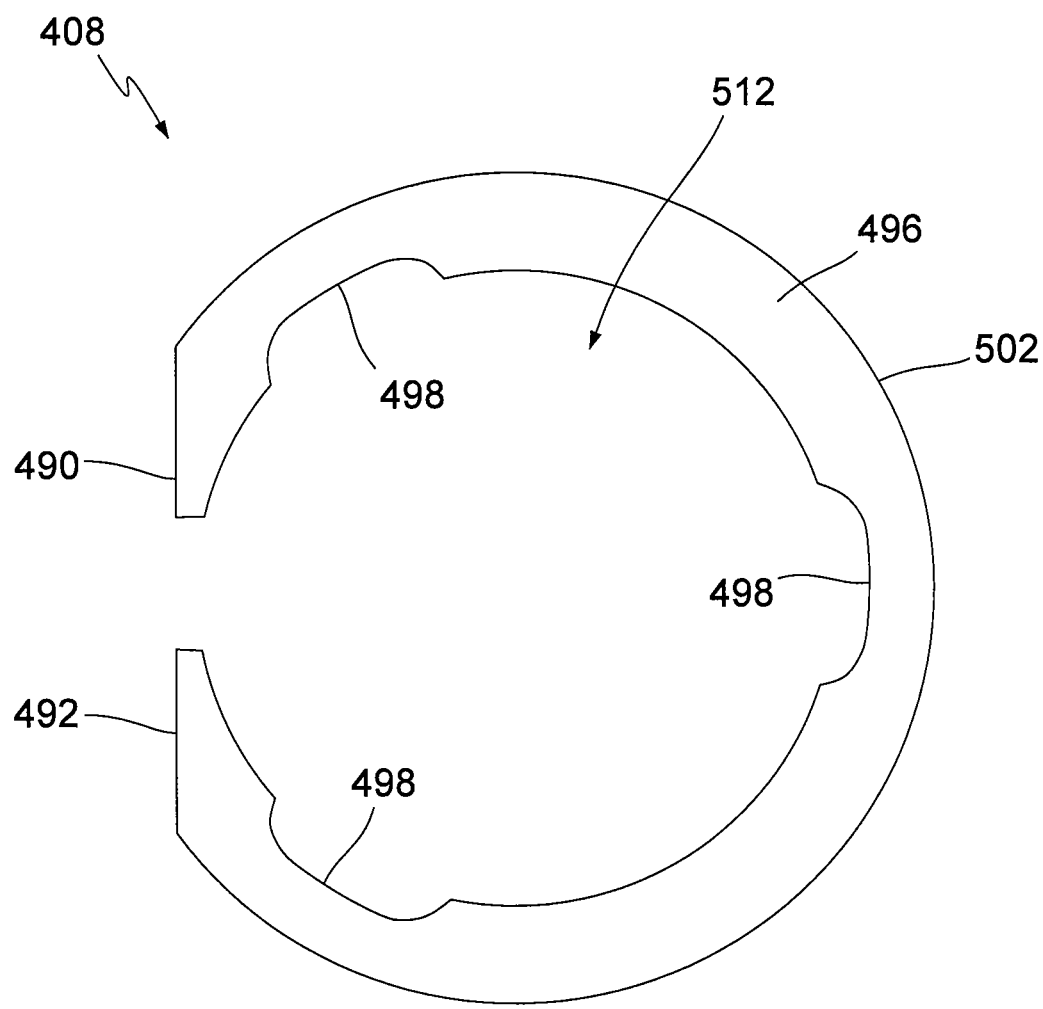
FIG. 44 is a top view of an exemplary retainer ring of the embodiment of FIG. 30.
Figure 45:
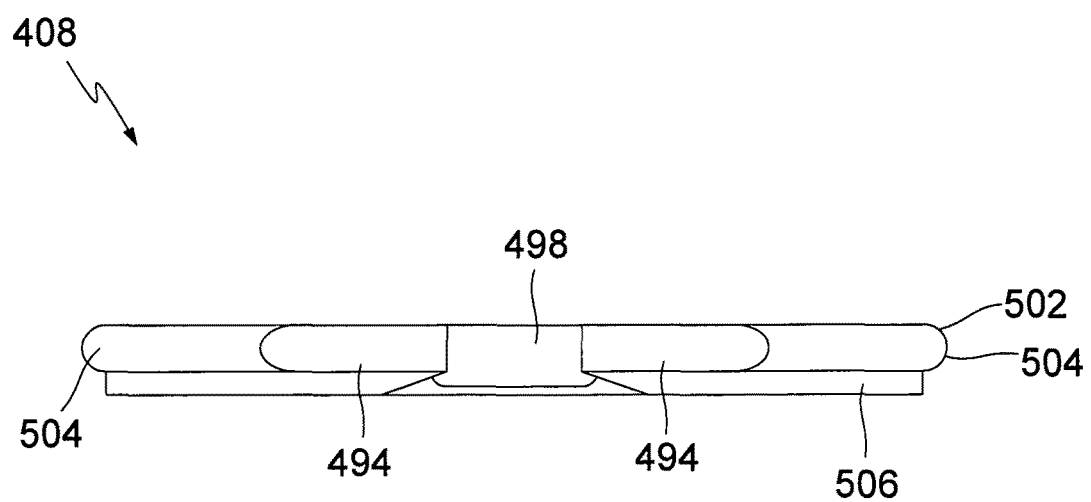
FIG. 45 is a profile view of the exemplary retainer ring of FIG. 44.
Figure 46:
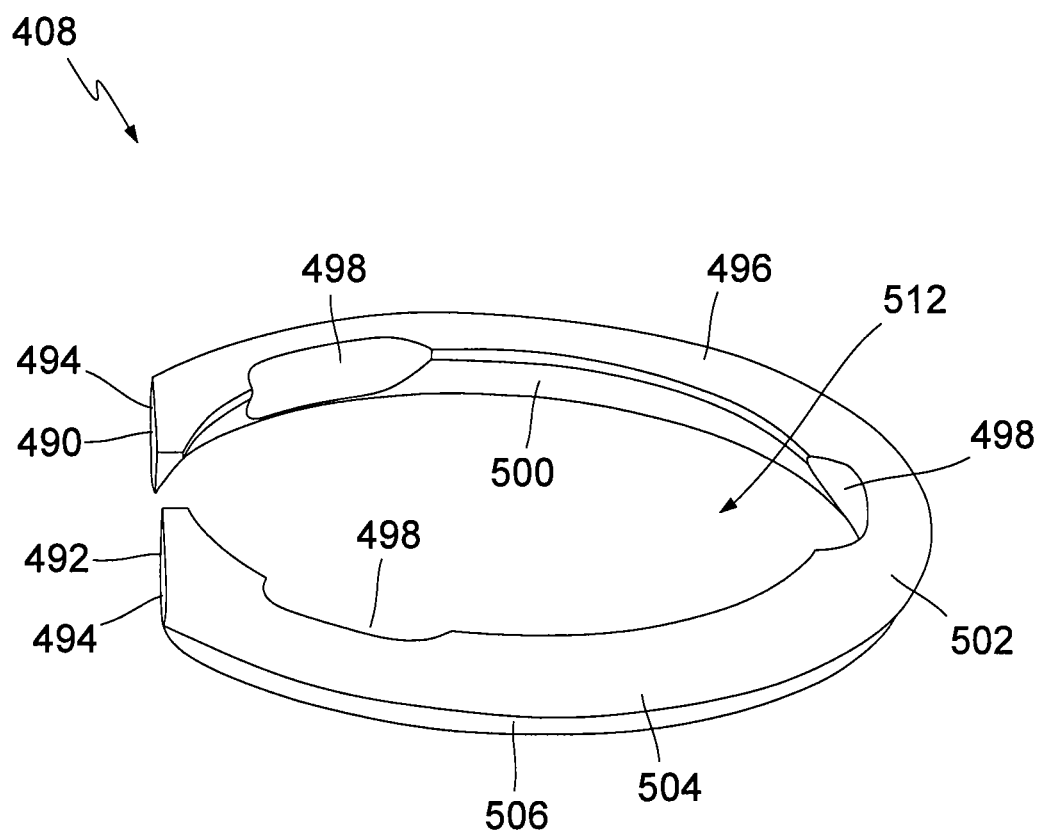
FIG. 46 is an elevated perspective view of the exemplary retainer ring of FIG. 44.
Figure 47:
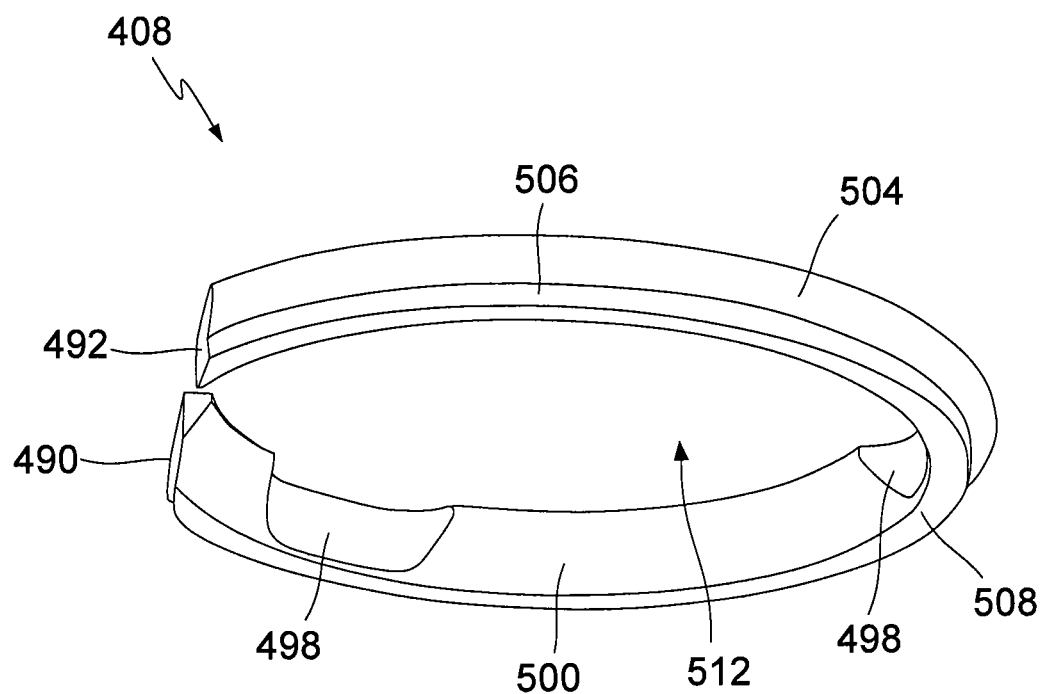
FIG. 47 is a bottom, perspective view of the exemplary retainer ring of FIG. 44.

Referencing FIGS. 41-43, the threaded pressing washer 406 comprises a ring-shaped body having a continuous wall 470 with a substantially flat, bottom surface 472. The bottom surface 472 transitions into a generally dome-shaped outer circumferential surface 474 and an inner circumferential surface 476. The continuous wall 470 embodies a wall thickness that increases from a maximum at the bottom surface 472, to a minimum at the top surface 478. In vertical cross-section, from top to bottom, the continuous wall 470 embodies a generally triangular shape with the base of the triangle comprising the bottom surface 472 and the apex of the triangle comprising the top surface 478. In between the top and bottom surfaces 472, 478, the outer circumferential surface 474 embodies a vertically arcuate shape and is substantially circular in horizontal cross-section, but for a series of projections 480 extending radially from the outer circumferential surface. In this exemplary embodiment, each projection 480 comprises a generally rectangular projection and three projections 480 are equidistantly spaced about the circumference of the threaded washer 406. Opposite the projections 480, on the inner circumferential surface 476, are threads 482 extending into a circular opening 484 within the interior of the threaded washer 406. These threads 482 are adapted to engage the threaded head of the screw 410 as will be discussed below.

Referencing FIGS. 44-47, the locking ring 408 comprises a semi-circular body having opposed open ends 490, 492. Each end 490, 492 is a mirror image of the other end and includes a vertical, planar side surface 494. The planar side surface 494 is perpendicular to a planar top surface 496 embodying a semi-circular shape. The circumferential width of the top surface 496 is substantially constant, but for three notches 498 formed axially through the top surface along an inner circumferential surface 500. By way of summary, the notches 498 mirror, but are slightly oversized with respect to, the projections 480 of the threaded washer 406. A circumferential edge 502 of the top surface 496 is rounded over to define a semi-circular rim 504 that transitions into a recessed circumferential vertical surface 506. This vertical surface 506 is perpendicular to a bottom surface 508 that circumferentially extends between the ends 490, 492. In this exemplary embodiment, the top surface 496 is oriented in parallel to the bottom surface 508 so that the arcuate interior surface 500 interposes the surfaces 496, 508. The arcuate interior surface 500 is curved so that the diameter of an opening 512, which extends vertically through the locking ring 408, decreases from the bottom surface 508 to just beneath the top surface 496. However, where the notches 498 are located within the top surface 496, these notches vertically extend into the interior surface 500 so that the notches do not exhibit the arcuate shape of the remainder of the interior surface.

Figure 48:
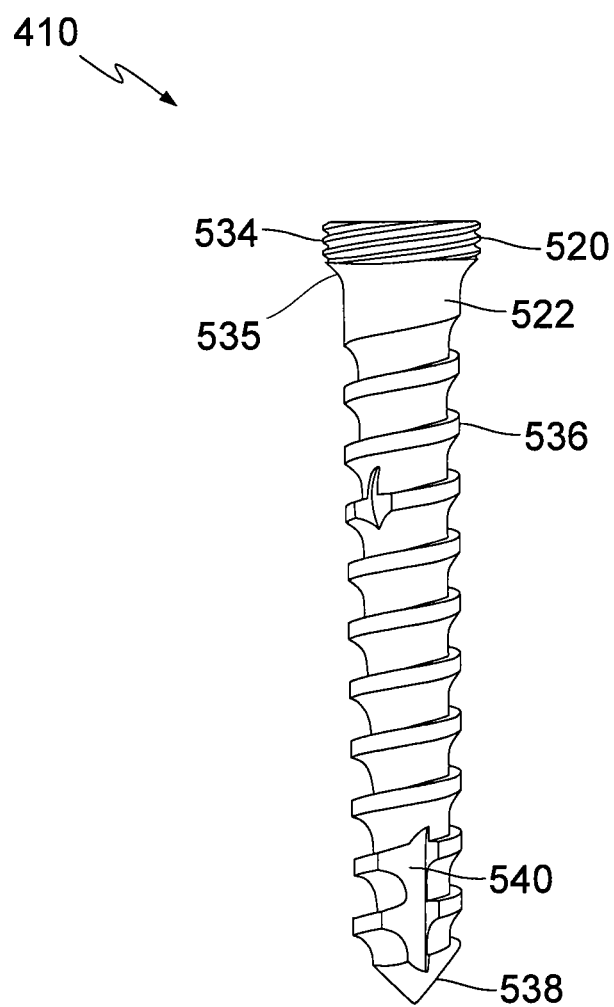
FIG. 48 is a profile view of an exemplary screw of the embodiment of FIG. 30.
Figure 49:
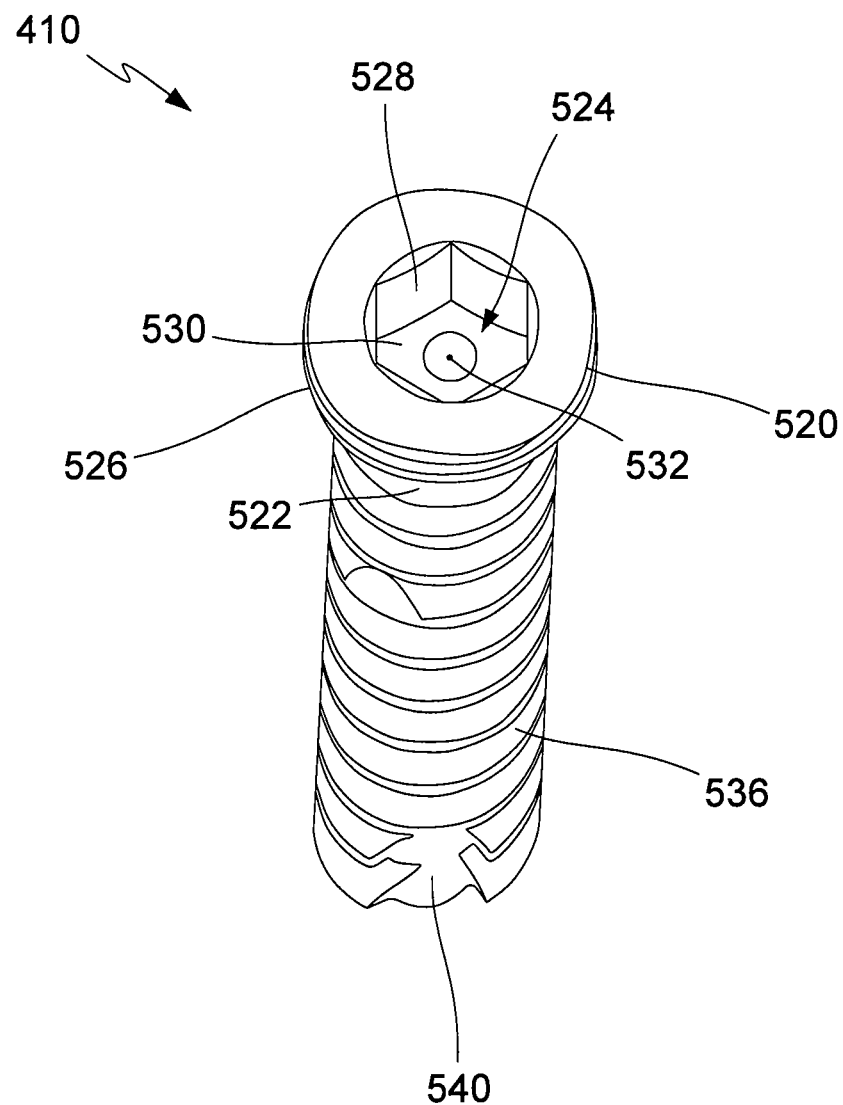
FIG. 49 is an elevated perspective view of the exemplary screw of FIG. 48.

Referencing FIGS. 48 and 49, the screw 410 comprises a head 520 and a shaft 522 extending from the head. The head 520 includes a cavity 524 centrally located and spaced from an outer circumferential surface 526. The cavity 524 is partially defined by a series of vertical surfaces 528 oriented in a hexagonal pattern that perpendicularly intersect a horizontal floor 530. The horizontal floor 530 includes a central conical depression 532, which is also part of the cavity 524. Threads 534 extend from the outer circumferential surface 526 of the head 520 and are adapted to engage the threads 482 of the threaded washer 406. Just below the threads 534, the head 520 includes an exterior surface 535 that tapers inward to join the shaft 522. Just below the tapering portion, the shaft 522 includes helical threads 536 that extend almost the entire length of the shaft to a conical tip 538. In this exemplary embodiment, the helical threads 536 include at least one discontinuity 540 proximate the conical tip 538 to facilitate aligning the screw 410 with a hole within the biologic substrate 412.

Referencing FIGS. 30-49, the fourth exemplary variable angle locking screw assembly 400 may be utilized to secure the biologic substrate 412, such as human bone, in a constant position for proper healing. An exemplary procedure for securing the substrate 412 to the base plate 402 may include drilling a hole into the substrate 412 at a desired angular orientation, where the hole has a diameter less than the diameter of the helical threads 536 on the shaft 522 of the screw 410. Prior to mounting the screw 410 to the substrate 412, the remaining components of the variable angle locking screw assembly 400 are mounted to the base plate 402.

By way of example, the base plate 402 is oriented so that the upper tray 414 is accessible, specifically at least one of the through holes 420. With the upper tray 414 oriented to face upward and exposing the entire length of the circumferential wall 422, the positioning washer 404 is first inserted into the through hole 420. More specifically, the rounded bottom surface 456 of the washer 404 is inserted into the through hole 420 first, followed by the top surface 452 of the washer. This orientation ensures that the rounded circumferential surface 454 of the washer 404, which transitions into the bottom surface 456, is adjacent and seated within the arcuate wall 430 of the second wall segment 428. When the washer 404 is seated adjacent to the arcuate wall 430, the top surface 452 is slightly recessed below the second arcuate wall 434. After the washer 404 is installed within the circumferential wall 422, the threaded pressing washer 406 is next installed.

The threaded washer 406 is inserted within the circumferential wall 422 so that the bottom surface 472 enters the circumferential wall first, followed by the top surface 478. Vertical lowering of the threaded washer 406 within the circumferential wall 422 continues until the bottom surface 472 sits upon the top surface 452 of the washer 404. But before the bottom surface 472 can sit upon the top surface 452 of the washer 404, the projections 480 on the outer circumferential surface 474 of the threaded washer 406 are aligned with the cut-outs 432 formed within arcuate wall 430 of the second segment 428. After the projections 480 are aligned with the cut-outs 432, the threaded washer 406 may be lowered within the circumferential wall 422 so that the bottom surface 472 sits upon the top surface 452 of the washer 404. Because the projections 480 are seated within the cut-outs 432, rotation of the threaded washer 406 with respect to the base plate 402 is inhibited. As soon as the bottom surface 472 of the threaded washer 406 sits upon the top surface 452 of the washer 404, the locking ring 408 may be inserted within the circumferential wall 422.

Insertion of the locking ring 408 within the circumferential wall 422 begins with inserting the bottom surface 508 first, followed by the top surface 496. Because the locking ring 408 is not circular, only a single rotational orientation is possible to install the locking ring within the circumferential wall 422 the base plate 402. Just before the locking ring 408 is inserted within the circumferential wall 422, the vertical side surface 494 is oriented in parallel to the vertical wall 440 of the circumferential wall. This orientation also inherently aligns the notches 498 with the cut-outs 432 of the circumferential wall 422. After the locking ring 408 has been aligned, it may be lowered so that the bottom surface 508 is proximate the ledge 438. But before the bottom surface 508 can reach the ledge 438, the locking ring 408 is circumferentially compressed to reduce the outside diameter of the locking ring, which can be accomplished because of the space between the open ends 490, 492. Reduction in the outside diameter of the locking ring 408 allows the semi-circular rim 504 to pass vertically beyond the top beveled edge 444 of the through hole 420. After passing the top beveled edge 444, the semi-circular rim 504 of the locking ring 408 rides upon the circumferential wall 422 just above the semicircular depression 446. But when the semi-circular rim 504 of the locking ring 408 reaches the semicircular depression 446, the inherent spring in the locking ring forces the semi-circular rim outward and into the semicircular depression, thereby mounting the locking ring securely to the base plate 402. After the locking ring 408 is seated within the semicircular depression 446, it is not possible to remove the washer 404 and/or the threaded washer 406 from the through hole 420.

After the washer 404, the threaded washer 406, and the locking ring 408 are inserted within the circumferential wall 422, a surgeon may then insert a drill bit (not shown) into the through hole 420 to contact the biologic substrate 412, such as human bone. At this time, the surgeon controls the drill bit to create a hole within the substrate 412 that will ultimately receive the screw 410 in order to mount the base plate 402 to the substrate 412. After the drill bit has completed boring the hole within the substrate 412, the drill bit is withdrawn from the substrate 412 and the through hole 420.

After removing the drill bit, the screw 410 may be inserted through the openings 458, 484, 512 with the conical tip 538 first, followed by the remainder of the shaft 522 or at least as much of the shaft as is necessary so the tip 538 reaches the hole within the biologic substrate 412. Because the diameter of the helical threads 536 is less than the diameter of the openings 458, 484, 512 extending through the washer 404, the threaded washer 406, and the locking ring 408, the shaft 522 passes right through the openings. In addition, the construction of the variable angle locking screw assembly 400 allows the screw to be oriented at angles other than axially aligned with circumferential wall 422 of the base plate 402 to reach the hole within the biologic substrate 412.

Generally, the threads 534 on the outer circumferential surface 526 of the screw head 520 initially engage the threads 482 on the inner circumferential surface 476 of the threaded washer 406 at approximately the same time as the tip 538 reaches the hole within the biologic substrate 412. At this point, the screw 410 is rotated by inserting a driver (not shown) into the cavity 524 and rotating the driver. Rotation of the screw 410 in the clockwise direction is operative to pull the shaft 522 into the biologic substrate 412 and to draw the threaded washer 406 upward vertically along the shaft 522 and also vertically within the through hole 420. This upward vertical motion of the threaded washer 406, while creating a gap (compare FIGS. 31 and 32) between the bottom surface 472 of the threaded pressing washer 406 and the top surface 452 of the washer 404, also operates to draw the outer circumferential surface 474 of the threaded washer 406 closer to the arcuate interior surface 500 of the locking ring 408. Eventually, clockwise rotation of the screw 410 (generally around 1-3 rotations of the screw, for example) causes the outer circumferential surface 474 of the threaded washer 406 to contact the arcuate interior surface 500 of the locking ring 408, thus creating a compression joint between the second wall section 466 of the washer 404 and the exterior tapered surface 535 of the screw 410, thereby inhibiting further rotation of the screw 410 with respect to the washer 404. At the same time, the compression joint is also formed between the threaded washer 406 and the locking ring 408. In order to discontinue the compression joints, the screw 410 is rotated in the counterclockwise direction, thereby allowing reversing the foregoing process.

The aforementioned components may, in exemplary from, be manufactured from titanium or stainless steel. However, it should be understood that any suitable material may be utilized to fabricate the aforementioned components including, without limitation, plastics, ceramics, metals, and alloys of the foregoing.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of mounting a base plate to an underlying biological substrate, the method comprising:
    coupling a nut within a first through hole disposed in a base plate, the first through hole defining a first longitudinal axis extending the length thereof, the first through hole at least partially defined by a flange having an interior circumferential wall, the base plate including a first anti-rotation feature, and the nut comprising:
       (a) a cylindrical inner wall at least partially defining a second through hole, the cylindrical inner wall being at least partially threaded, and the second through hole defining a second longitudinal axis extending the length thereof,
       (b) an engaging wall extending from a first end of the nut, the engaging wall at least partially circumscribing and extending towards an opposing second end of the nut,
       (c) a projection extending radially outward from the second end of the nut, the projection having a widthwise dimension greater than a diameter of the first through hole, wherein the flange is at least partially received between the engaging wall and an outer wall of the nut to couple the nut within the first through hole; and
       (d) a washer having a widthwise dimension greater than the diameter of the first through hole, wherein the projection and the washer cooperate to retain at least a portion of the nut within the first through hole;
    wherein the nut is selectively rotatable within the first through hole of the base plate about and between 0 degrees and a maximum angle between the first and second longitudinal axes, and wherein the nut includes a second anti-rotation feature that is engageable with the first anti-rotation feature of the base plate to inhibit rotation of the nut with respect to the base plate in a plane perpendicular to one of the first and second axes;
    inserting a screw into each of the first and second through holes so that at least a portion of a shaft of the screw extends beyond the interior circumferential wall of the base plate, where at least a head of the screw is retained within the first and second through holes, wherein the shaft comprises a first threaded portion and a second threaded portion, the first threaded portion having a first diameter and the second threaded portion having a second diameter that is greater than the first diameter, the second threaded portion being located between the head and the first threaded portion, and wherein the first threaded portion is insertable at a selected angle about and between 0 degrees and a maximum angle relative to the first longitudinal axis;
    advancing the shaft of the screw through the second through hole to threadably engage the second threaded portion of the shaft of the screw with the nut;
    rotationally advancing the second threaded portion of the screw with respect to the nut so that the head of the screw and the engaging wall of the nut are urged into compressive engagement with the flange and secure the selected angle of the first threaded portion.

2. The method of claim 1, wherein the maximum angle is about 15 degrees.

3. The method of claim 1, further comprising inserting a locking ring into the first through hole of the base plate, the locking ring being engageable with a locking ring channel disposed in the interior circumferential wall subsequent to engaging the nut within the first through hole.

4. A method of mounting a base plate to an underlying biological substrate, the method comprising:
    coupling a washer nut within a first through hole disposed in the base plate, the first through hole defining a first longitudinal axis extending the length thereof, the washer nut having a second through hole disposed therein defining a second longitudinal axis extending the length thereof and a circumferential recess disposed on an outer surface thereof that receives and retains at least a portion of the base plate, wherein the circumferential recess includes a projection extending radially from a second end of the nut and an engaging wall extending from a first end of the nut towards the second end of the nut, wherein the projection has a widthwise dimension that is greater than a diameter of the first through hole to retain at least a portion of the washer nut within the first through hole, wherein a flange that at least partially defines the first through hole is received between the engaging wall and an outer wall of the nut, wherein the washer nut is axially and angularly repositionable with respect to the first through hole;
    inserting a screw into each of the first and second through holes so that at least a portion of a shaft of the screw extends beyond the first through hole disposed in the base plate, wherein at least a head of the screw is retained within the first and second through holes, wherein the shaft comprises a first threaded portion and a second threaded portion, the first threaded portion having a first diameter and the second threaded portion having a second diameter that is greater than the first diameter, the second threaded portion being located between the head and the first threaded portion, and wherein the first threaded portion is insertable at a selected angle about and between 0 degrees and a maximum angle with respect to the first and second longitudinal axes;
    advancing the shaft of the screw with respect to the second through hole of the washer nut to thread ably engage the second threaded portion of the threaded shaft of the screw with the washer nut; and rotationally advancing the second threaded portion with respect to the washer nut so that the head of the screw and the washer nut are urged into compressive engagement with the base plate and secure the selected angle of the first threaded portion.

5. The method of claim 4, wherein the maximum angle is about 15 degrees.

6. The method of claim 4, further comprising inserting a locking ring into the first through hole of the base plate, the locking ring being engageable with a locking ring channel disposed in the interior circumferential wall subsequent to engaging the nut within the first through hole.

7. The method of claim 4, wherein rotationally advancing the second portion of the screw with respect to the nut further comprises forming a compression joint between the head of the screw and the washer nut.

8. A method of mounting a base plate to an underlying biological substrate, the method comprising:

coupling a washer nut within a first through hole disposed in the base plate, the first through hole at least partially defined by a flange having an interior circumferential wall tapered to decrease a diameter of the interior circumferential wall from a first surface towards an opposed second surface of the base plate, the washer nut defining a second through hole that is at least partially threaded, and the washer nut comprising a circumferential recess on an outer surface thereof that receives at least a portion of the flange, wherein the circumferential recess includes a projection extending radially from a second end of the nut and an engaging wall extending from a first end of the nut towards the second end of the nut, wherein the projection has a widthwise dimension that is greater than a diameter of the first through hole to retain at least a portion of the washer nut within the first through hole;

inserting a locking ring into the first through hole of the base plate, the locking ring being engageable with a locking ring channel disposed in the interior circumferential wall, and the locking ring at least partially defining a third through hole;

inserting a screw into and at least partially through each of the first, second, and third through holes so that at least a portion of a shaft of the screw extends beyond the interior circumferential wall of the base plate, wherein at least a head of the screw is retained within the first through hole, wherein the shaft comprises a first threaded portion and a second threaded portion, the first threaded portion having a first diameter and the second threaded portion having a second diameter that is greater than the first diameter, the second threaded portion being located between the head and the first threaded portion, and wherein the first threaded portion is insertable at a selected angle about and between 0 degrees and a maximum angle relative to an axis defined by one of the first and second through holes;

advancing the shaft of the screw with respect to the second through hole of the washer nut to threadably engage the second threaded portion of the threaded shaft of the screw with the washer nut; and rotationally advancing the second threaded portion with respect to the washer nut to urge the washer nut against the locking ring to secure the screw at the selected angle.

9. The method of claim 8, wherein the maximum angle is about 15 degrees.

10. A method of mounting a base plate to an underlying biological substrate, the method comprising:

coupling a washer nut within a first through hole disposed in the base plate, the first through hole at least partially defined by a flange having an interior circumferential wall tapered to decrease a diameter of the interior circumferential wall from a first surface towards an opposed second surface of the base plate, the washer nut defining a second through hole that is at least partially threaded, and the washer nut comprising a circumferential recess on an outer surface thereof that receives at least a portion of the flange; wherein the circumferential recess includes a projection extending radially from a second end of the nut and an engaging wall extending from a first end of the nut towards the second end of the nut, wherein the projection has a widthwise dimension that is greater than a diameter of the first through hole to retain at least a portion of the washer nut within the first through hole;

inserting a screw into and at least partially through each of the first and second through holes so that at least a portion of a shaft of the screw extends beyond the interior circumferential wall of the base plate, wherein at least a head of the screw is retained within the first through hole, and wherein the shaft is insertable at a selected angle about and between 0 degrees and a maximum angle relative to an axis defined by one of the first and second through holes;

advancing the shaft of the screw with respect to the second through hole of the washer nut to urge the washer nut against the locking ring to secure the screw at the selected angle.

11. The method of claim 10, wherein the maximum angle is about 15 degrees.

12. The method of claim 10, further comprising inserting a locking ring into the first through hole of the base plate, the locking ring being engageable with a locking ring channel disposed in the interior circumferential wall subsequent to engaging the nut within the first through hole.

13. The method of claim 10, wherein the shaft comprises a first threaded portion and a second threaded portion, the first threaded portion having a first diameter and the second threaded portion having a second diameter that is greater than the first diameter, the second threaded portion being located between the head and the first threaded portion.

14. The method of claim 13, wherein the first threaded portion is insertable at the selected angle.

15. The method of claim 14, wherein advancing the shaft of the screw with respect to the second through hole further comprises rotationally advancing the second threaded portion with respect to the washer nut to urge the washer nut against the locking ring to secure the screw at the selected angle.

* * * * *